US011524971B2

(12) United States Patent
Hardimon et al.

(10) Patent No.: US 11,524,971 B2
(45) Date of Patent: Dec. 13, 2022

(54) DIVALENT METAL ASCORBATE GLYCINATE CO-SALT

(71) Applicant: JOST CHEMICAL CO., St. Louis, MO (US)

(72) Inventors: Joseph R. Hardimon, Belleville, IL (US); Kasey L. Morris, Florissant, MO (US); Kevin D. Jerome, St. Charles, MO (US)

(73) Assignee: Jost Chemical Co., St. Louis, MO (US)

( * ) Notice: Subject to any disclaimer, the term of this patent is extended or adjusted under 35 U.S.C. 154(b) by 0 days.

(21) Appl. No.: 17/634,480

(22) PCT Filed: Jul. 12, 2021

(86) PCT No.: PCT/US2021/041302
§ 371 (c)(1),
(2) Date: Feb. 10, 2022

(87) PCT Pub. No.: WO2022/015654
PCT Pub. Date: Jan. 20, 2022

(65) Prior Publication Data
US 2022/0298177 A1    Sep. 22, 2022

Related U.S. Application Data

(60) Provisional application No. 63/053,293, filed on Jul. 17, 2020.

(51) Int. Cl.
| C07F 3/06 | (2006.01) |
| C07D 307/62 | (2006.01) |
| C07F 3/04 | (2006.01) |
| C07F 3/02 | (2006.01) |

(52) U.S. Cl.
CPC .............. *C07F 3/06* (2013.01); *C07D 307/62* (2013.01); *C07F 3/02* (2013.01); *C07F 3/04* (2013.01)

(58) Field of Classification Search
None
See application file for complete search history.

(56) References Cited

U.S. PATENT DOCUMENTS

| 2011/0237813 A1 | 9/2011 | Gleason et al. |
| 2021/0188755 A1 | 6/2021 | Hardimon et al. |

FOREIGN PATENT DOCUMENTS

| CN | 113121375 A | 7/2021 |
| WO | 2003049850 A2 | 6/2003 |

OTHER PUBLICATIONS

International Search Report for PCT/US2021/041302 dated Oct. 27, 2021.
Written Opinion for PCT/US2021/041302 dated Oct. 27, 2021.
Mossad S, Macknin M, Mendendorp S, et al. Zinc Gluconate Lozenges for Treating the Common Cold: A Randomized, Double-Blind, Placebo-Controlled Study. Annals of Internal Medicine Jul. 15, 1996.
Te Velthuis AJW, van den Worm She, Sims AC, Baric RS, Snijder EJ, van Hemert MJ (2010) Zn2+ Inhibits Coronavirus and Arterivirus RNA Polymerase Activity In Vitro and Zinc Ionophores Block the Replication of These Viruses in Cell Culture. PLoS Pathog 6(11): e1001176. (10 Pages).
Shankar AH, Prasad AS. Zinc, and immune function: the biological basis of altered resistance to infection Am J Clin Nutr. Aug. 1998;68(2 Suppl):447S-463S (17 Pages).
Singh M, Das RR. Zinc for the common cold. Cochrane Database of Systematic Reviews 2013, Issue 6 Art. No. CD001364. DOI: 10.1002/14651858.CD001364.pub4 (72 Pages).
Liguori, I., Russo, G., Curcio, F., Bulli, G., Aran, L., Della-Morte, D., Gargiulo, G., Testa, G., Cacciatore, F., Bonaduce, D., & Abete, P. (2018). Oxidative stress, aging, and diseases. Clinical Interventions in Aging, 13, 757-772 (16 Pages).
Persaud, C., Forrester, T., & Jackson, A. A. (1996). Urinary excretion of 5-L-oxoproline (pyroglutamic acid) is increased during recovery from severe childhood malnutrition and responds to supplemental glycine. The Journal of Nutrition, 126(11), 2823-2830 (8 Pages).
McCarty, M. F., O'Keefe, J. H., & DiNicolantonio, J. J. (2018). Dietary Glycine is Rate-Limiting for Glutathione Synthesis and May Have Broad Potential for Health Protection. The Ochsner journal, 18(1), 81-87.
Branch J. D. (2003). Effect of creatine supplementation on body composition and performance: a meta-analysis. International Journal of Sport Nutrition and Exercise Metabolism, 13(2), 198-226. https://doi.org/10.1123/jsnem.13.2.198 (31 Pages).
Chilibeck, P. D., Kaviani, M., Candow, D. G., & Zello, G. A. (2017). Effect of creatine supplementation during resistance training on lean tissue mass and muscular strength in older adults: a meta-analysis. Open Access Journal of Sports Medicine, 8, 213-226. https://doi.org/10.2147/OAJSM.S123529 (14 Pages).
Avgerinos, K. I., Spyrou, N., Bougioukas, K. I., & Kapogiannis, D. (2018). Effects of creatine supplementation on cognitive function of healthy individuals: A systematic review of randomized controlled trials. Experimental Gerontology, 108, 166-173 (8 Pages).
Kreider, R. B., Kalman, D. S., Antonio, J., Ziegenfuss, T. N., Wildman, R., Collins, R., Candow, D. G., Kleiner, S. M., Almada, A. L., & Lopez, H. L. (2017). International Society of Sports Nutrition position stand: safety and efficacy of creatine supplementation in exercise, sport, and medicine. Journal of the International Society of Sports Nutrition, 14, 18 (18 Pages).
Kalhan, S. C., Gruca, L., Marczewski, S., Bennett, C., & Kummitha, C. (2016). Whole body creatine and protein kinetics in healthy men and women: effects of creatine and amino acid supplementation. Amino Acids, 48(3), 677-687 (11 Pages).

(Continued)

*Primary Examiner* — Joseph R Kosack
(74) *Attorney, Agent, or Firm* — Sandberg Phoenix & von Gontard PC

(57) ABSTRACT

A zinc ascorbate glycinate co-salt having a formula of $MC_8H_{11}NO_8$ and a suggested structure of: Formula (I). Where M is Ca, Mg, or Zn. The divalent metal ascorbate glycinate co-salt is formed as a powder having a metal content of about 8% to about 21% on an anhydrous basis and containing between 0.0-20.0% water.

4 Claims, 22 Drawing Sheets

(56) References Cited

OTHER PUBLICATIONS

González-Ortiz, M., Medina-Santillán, R., Martínez-Abundis, E., & von Drateln, C. R. (2001). Effect of glycine on insulin secretion and action in healthy first-degree relatives of type 2 diabetes mellitus patients. Hormone and Metabolic Research, 33(6), 358-360 (3 Pages).

Proksch, E., Segger, D., Degwert, J., Schunck, M., Zague, V., & Oesser, S. (2014). Oral supplementation of specific collagen peptides has beneficial effects on human skin physiology: a double-blind, placebo-controlled study. Skin Pharmacology and Physiology, 27(1), 47-55 (10 Pages).

Clark, K. L., Sebastianelli, W., Flechsenhar, K. R., Aukermann, D. F., Meza, F., Millard, R. L., Deitch, J. R., Sherbondy, P. S., & Albert, A. (2008). 24-Week study on the use of collagen hydrolysate as a dietary supplement in athletes with activity-related joint pain. Current Medical Research and Opinion, 24(5), 1485-1496. https://doi.org/10.1185/030079908x291967 (13 Pages).

Elam, M. L., Johnson, S. A., Hooshmand, S., Feresin, R. G., Payton, M. E., Gu, J., & Arjmandi, B. H. (2015). A calcium-collagen chelate dietary supplement attenuates bone loss in postmenopausal women with osteopenia: a randomized controlled trial. Journal of Medicinal Food, 18(3), 324-331. https://doi.org/10.1089/jmf.2014.0100 (8 Pages).

Bannai, M., & Kawai, N. (2012). New therapeutic strategy for amino acid medicine: glycine improves the quality of sleep. Journal of Pharmacological Sciences, 118(2), 145-148 (4 pages).

Kawai, N., Sakai, N., Okuro, M., Karakawa, S., Tsuneyoshi, Y., Kawasaki, N., Takeda, T., Bannai, M., & Nishino, S. (2015). The sleep-promoting and hypothermic effects of glycine are mediated by NMDA receptors in the suprachiasmatic nucleus. Neuropsychopharmacology: Official Publication of the American College of Neuropsychopharmacology, 40(6), 1405-1416 (12 Pages).

SEM Imaging of Zinc Bis-Glycinate

SEM Imaging of Zinc Ascorbate

SEM Imaging of Zinc Ascorbate Glycinate Co-Salt

FT-IR Comparisons of calcium ascorbate glycinate co-salt vs. calcium ascorbate, calcium bisglycinate and a 1:1 dry mix of calcium ascorbate and calcium bisglycinate

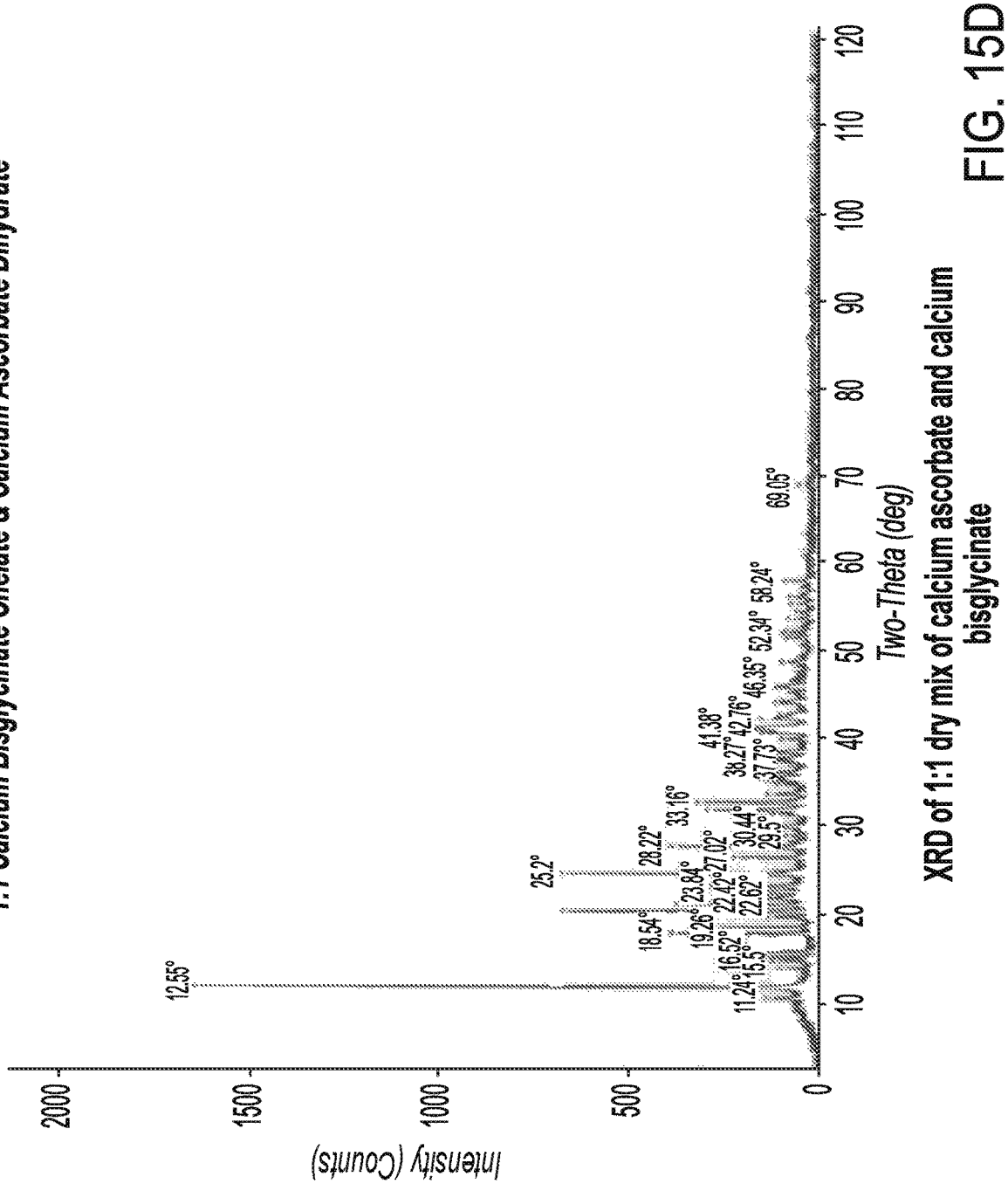

FT-IR Comparisons of magnesium ascorbate glycinate co-salt
vs. magnesium ascorbate, magnesium bisglycinate and a 1:1 dry mix of
magnesium ascorbate and magnesium bisglycinate

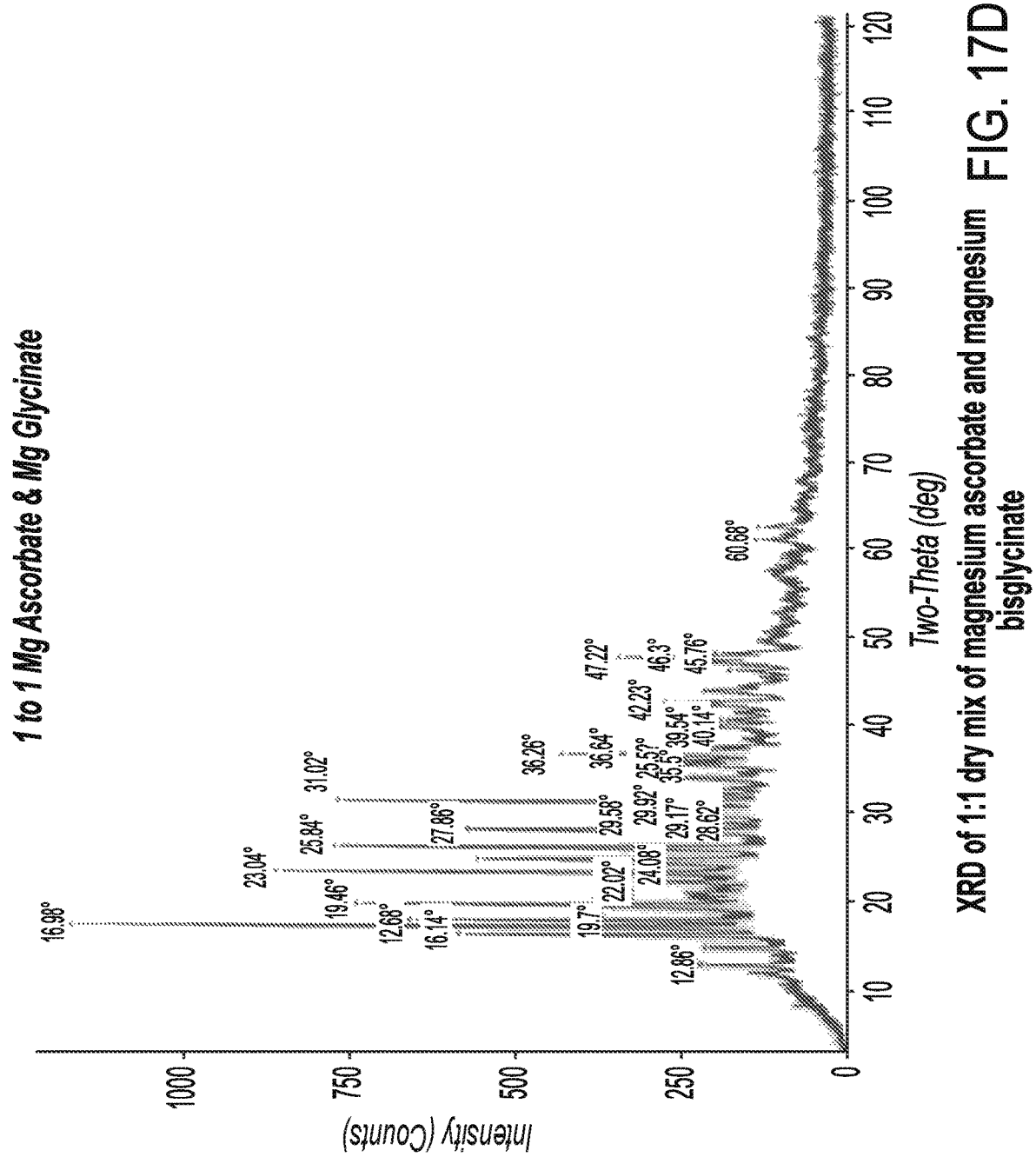

DIVALENT METAL ASCORBATE GLYCINATE CO-SALT

CROSS-REFERENCE TO RELATED APPLICATIONS

This application is the US National Stage application under 35 USC § 372 of International App. No. PCT/US2021/041302 filed Jul. 12, 2021 which, in turn, claims priority to U.S. App. No. 63/053,293, filed Jul. 17, 2020, entitled Zinc Ascorbate Glycinate Co-Salt, and which is incorporated herein by reference.

STATEMENT REGARDING FEDERALLY SPONSORED RESEARCH OR DEVELOPMENT

Not Applicable.

BACKGROUND

This application relates to a novel divalent metal ascorbate glycinate co-salt compound, which incorporates an equal molar ratio of ascorbic acid and glycine, completely neutralized with a divalent metal in a metal to ligand ratio (i.e., a metal:ascorbate:glycinate ratio) of 1:1:1.

Divalent metals, such as calcium, magnesium, and zinc, are important for human health. The importance of calcium in cellular biochemistry is well known. Also well-known is the importance of trace minerals, such as magnesium, and zinc, to human health. For example, many studies show that zinc supplementation can lessen the severity of the common cold and is beneficial to the human immune system[1-4].

Other compounds are important as well. Glycine ($NH_2$—$CH_2$—COOH) is believed to be beneficial in reducing oxidative stress through production of glutathione in the body[5-7]. Further, glycine is used by the body to produce creatine, a substance shown to increase muscle size, strength, and power[8-10]. Glycine and has also been studied for its beneficial effects on bone health, brain function and neurological conditions like Parkinson's and Alzheimer's disease[7-10]. Glycine is a major constituent of collagen, which is known to promote skin health, relief of joint pain and prevention of bone loss[11-18]. Other studies also show that glycine may also benefit sleep quality and mental cognition[19-22]. The benefits of ascorbic acid (vitamin C) are well known and documented.

It would be desirable to provide a compound that can deliver both glycine and minerals, for example, by ingestion.

BRIEF SUMMARY

We have developed a new co-salt that delivers a divalent metal (such as $Ca^{+2}$, $Mg^{+2}$, or $Zn^{+2}$), ascorbic acid (vitamin C) and glycine in a single water-soluble dosage unit without the need for blending or combining multiple components.

Briefly, a divalent metal ascorbate glycinate co-salt, and hydrates thereof. As a hydrate, the divalent metal ascorbate glycinate co-salt has a formula of $MC_8H_{11}NO_8 \cdot XH_2O$. The co-salt, in anhydrous form, is believed to have the following general structure:

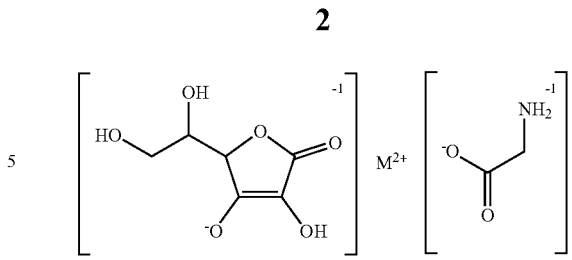

The zinc, magnesium, and calcium ascorbate glycinate co-salts are thus believed to have the following structures:

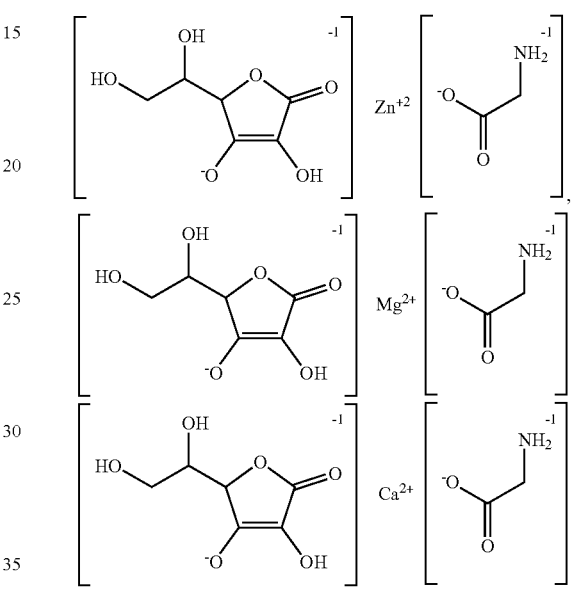

The molar quantity of ascorbic acid and glycine in the co-salt is 1:1 and the metal ligand, or metal:ascorbic acid:glycine, ratio is 1:1:1.

The divalent metal ascorbate glycinate co-salt has a metal content of about 8% to about 21% on an anhydrous basis.

Preferably, the divalent metal glycinate co-salt, when dried, is in powder form and contains up to about 20% water.

The source of metal for the co-salt is a metal, a metal oxide, a metal hydroxide or a metal carbonate. The preferred source of the metal depends on the metal chosen. A preferred zinc source, for example, is zinc oxide (ZnO). The co-salt (in aqueous form) wherein the source for the metal (M) is a metal oxide (MO) is defined by the following equation:

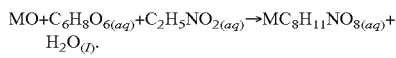

$$MO + C_6H_8O_{6(aq)} + C_2H_5NO_{2(aq)} \rightarrow MC_8H_{11}NO_{8(aq)} + H_2O_{(l)}.$$

The 1:1 molar ratio of citric acid and glycine in the aqueous solution is neutralized with a 90-110% 1 molar metal equivalence.

The neutralized solution is dried to a free-flowing powder.

BRIEF DESCRIPTION OF THE DRAWINGS

FIGS. 15A-D are XRD patterns of calcium ascorbate glycinate co-salt, calcium ascorbate, calcium bisglycinate, and a 1:1 dry mix of calcium ascorbate and calcium bisglycinate, respectively;

FIGS. 17A-D are XRD patterns of magnesium ascorbate glycinate co-salt, magnesium ascorbate, magnesium bisglycinate, and a 1:1 dry mix of magnesium ascorbate and magnesium bisglycinate, respectively.

Corresponding reference numerals will be used throughout the several figures of the drawings.

DETAILED DESCRIPTION

Figure 1:
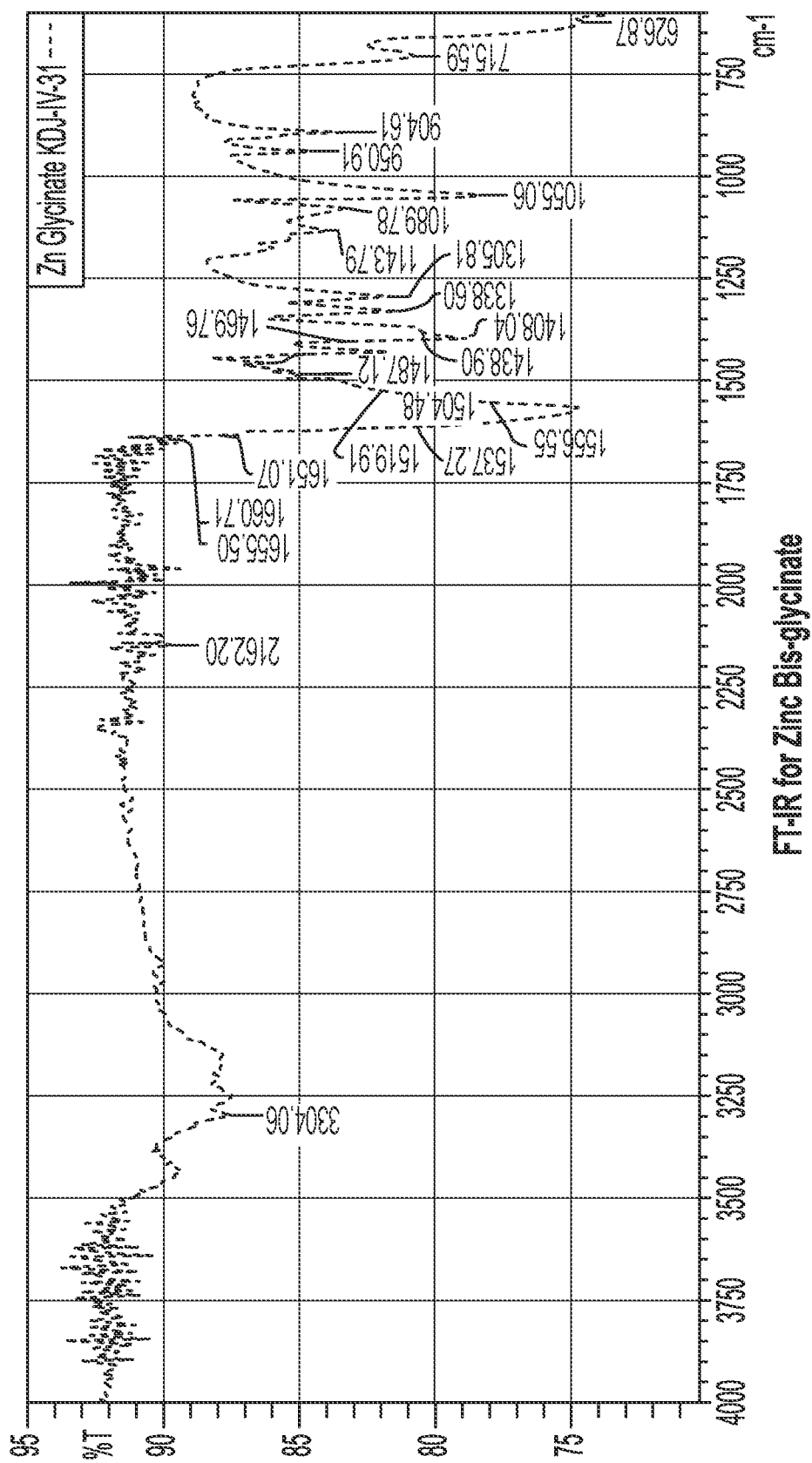
FIGS. 1 and 2 are infrared spectroscopy (FT-IR) spectra for Zinc Bis-glycinate and Zinc Ascorbate, respectively.

The following detailed description illustrates the claimed invention by way of example and not by way of limitation. This description will clearly enable one skilled in the art to make and use the claimed invention, and describes several embodiments, adaptations, variations, alternatives and uses of the claimed invention, including what we presently believe is the best mode of carrying out the claimed invention. Additionally, it is to be understood that the claimed invention is not limited in its application to the details of construction and the arrangements of components set forth in the following description or illustrated in the drawings. The claimed invention is capable of other embodiments and of being practiced or being carried out in various ways. Also, it is to be understood that the phraseology and terminology used herein is for the purpose of description and should not be regarded as limiting.

Several laboratory samples of the novel divalent metal ascorbate glycinate co-salt were prepared for use in demonstrating both matter of composition and comparative studies against both metal ascorbate and metal glycinate (i.e., zinc ascorbate and zinc glycinate).

An aqueous divalent metal ascorbate glycinate co-salt is formed by combining anhydrous ascorbic acid ($C_6H_8O_6$) and glycine ($C_2H_5NO_2$) in a 1:1 molar ratio, and neutralizing the aqueous solution with 90-110% of a 1 molar divalent metal equivalence. The metal source is the metal, a metal oxide, a metal hydroxide or a metal carbonate. Thus, for example, for a zinc ascorbate glycinate co-salt, the source for the zinc would be a zinc, zinc oxide, zinc hydroxide or zinc carbonate. The divalent metal ascorbate glycinate co-salt when prepared has a molecular formula of $MC_8H_9NO_8$ as shown below:

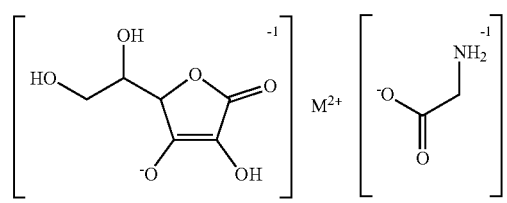

and is formed by the following basic reaction:

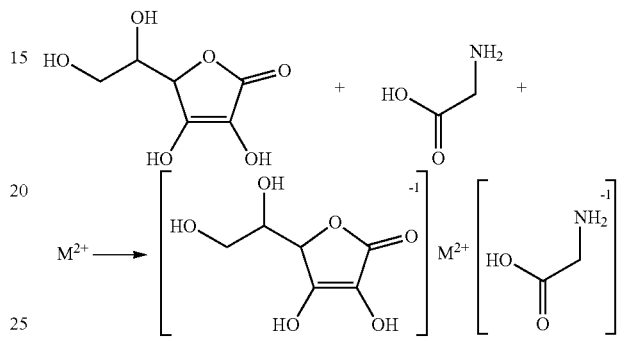

where M is Ca, Mg, or Zn derived from a metal, hydroxide, oxide or carbonate.

The production of an aqueous solution of the divalent metal ascorbate glycinate co-salt, wherein an oxide is the metal source, is shown in Equation 1 and by drying to a free-flowing powder in Equation 2.

$$MO + C_6H_8O_{6(aq)} + C_2H_5NO_{2(aq)} \rightarrow MC_8H_{11}NO_{8(aq)} + H_2O_{(l)} \qquad \text{Eq. 1:}$$

$$MC_8H_{11}NO_{8(aq)} \rightarrow MC_8H_{11}NO_8 \cdot XH_2O \text{ (Drying Step)} \qquad \text{Eq. 2:}$$

As is known, the value of X in Equation 2 above depends on the extent of drying of the co-salt during the drying step.

The divalent metal ascorbate glycinate co-salt is believed to have the following general structure:

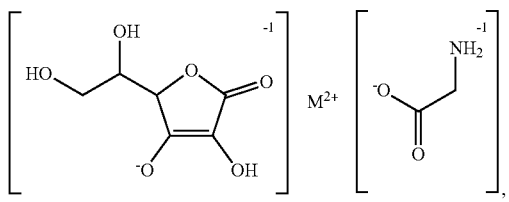

wherein M is Ca, Mg, and Zn.

The zinc, magnesium, and calcium ascorbate glycinate co-salts are thus believed to have the following structures:

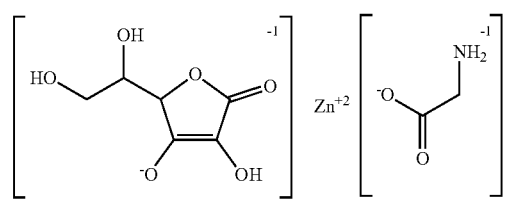

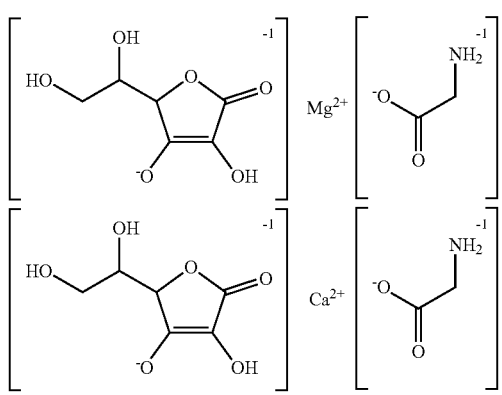

The anhydrous co-salts have molecular weights and a wt % metal content as shown in Table I below.

TABLE I

| Co-salt | mol weight (g/mol) | metal content wt % |
|---|---|---|
| Zinc ascorbate glycinate | 314.6 | 20.8 |
| Calcium ascorbate glycinate | 291.3 | 13.8 |
| Magnesium ascorbate glycinate | 273.5 | 8.9 |

The co-salt typically is found to contain between 0.0-20.0% water depending on extent of drying.

To demonstrate matter of composition and product superiority of the co-salts, classical chemistry methodology (assay), infrared spectroscopy (FT-IR), electron microscopy (SEM) and X-ray diffraction (XRD) were implemented.

EXAMPLES

1. Zinc Ascorbate Glycinate Co-Salt

A. Lab Scale Preparation of Zinc Ascorbate Glycinate Co-Salt.

A reaction mixture was prepared comprising 176.12 g (1 mol) anhydrous ascorbic acid and 75.01 g (1 mol) glycine dissolved in 1000 g of water. The mixture was heated to about 60-80° C. The resulting acid solution was neutralized with 81.4 g (1 mol) of zinc oxide and digested with agitation at about 60-80° C. until complete reaction was achieved (between 1-4 hours). The resulting reaction mass contained 314.56 g (1 mol) of zinc ascorbate glycinate co-salt having a metal to ligand (metal:ascorbate:glycine) ratio of 1:1:1 remaining in solution. The reaction mass was filtered to remove any unreacted zinc oxide and other extraneous matter. The filtrate was dried to produce a free-flowing powder containing zinc ascorbate glycinate co-salt having a metal to ligand ratio of 1:1:1 and a moisture content of 0.0-20.0%.

B. Pilot Plant Scale Preparation of Zinc Ascorbate Glycinate Co-Salt.

A reaction mixture was prepared comprising 3.52 Kg (20 mol) anhydrous ascorbic acid and 1.5 Kg (20 mol) glycine dissolved in 20 Kg of water. The mixture was heated to about 60-80° C. The resulting acid solution was neutralized with 1.6 Kg (20 mol) of zinc oxide and digested with agitation at about 60-80° C. until complete reaction was achieved (between 1-4 hours). The resulting reaction mass contained 6.3 Kg (20 mol) of zinc ascorbate glycinate co-salt having a metal to ligand ratio of 1:1:1 remaining in solution. The reaction mass was filtered to remove any unreacted zinc oxide and other extraneous matter. The filtrate was dried to produce a free-flowing powder containing zinc ascorbate glycinate co-salt having a metal to ligand ratio of 1:1:1 and a moisture content of 0.0-20.0%.

To assist in matter of composition and comparison, a dry blend was prepared by mixing 0.5 mole of zinc glycinate with 0.5 mole of zinc ascorbate. This sample will further be referred to as the "component dry blend" and will be used to help demonstrate the novel zinc ascorbate glycinate co-salt's composition.

Classical Chemistry Methodology

Research samples of zinc ascorbate glycinate co-salts lab scale sample A and pilot scale sample B were prepared and analyzed for zinc content using EDTA titration and Eriochrome Black T (EBT) indicator solution. The water content of both samples was determined by Thermogravimetric Analysis (TGA) so that the anhydrous zinc content could be calculated and compared to theoretical anhydrous magnesium content. The sample data shown in Table 2, below, shows the theoretical amount of zinc that is consistent with the zinc ascorbate glycinate co-salt formula.

TABLE 2

Zinc Content, Water Content and Theoretical Assay values for Zinc Ascorbate Glycinate Co-salts

| Sample | % Zn (as is) | % Water | % Zn Anhydrous | % of Theoretical Zn (20.8%) |
|---|---|---|---|---|
| A | 19.7% | 5.1% | 20.8% | 100% |
| B | 20.2% | 2.1% | 20.6% | 99% |

FT-IR Spectroscopy

Infrared spectroscopy shown in FIGS. 1-4 was employed to demonstrate the uniqueness of the zinc ascorbate glycinate co-salt against zinc glycinate, zinc ascorbate and the "component dry blend" described above. Zinc Bis-glycinate (FIG. 1) shows strong absorbances in the fingerprint region of 1560, 1400, 1050, 700 cm$^{-1}$ and distribution of strong absorbances between approximately 626 and 720 cm$^{-1}$.

Zinc Ascorbate (FIG. 2) has strong absorbances in the fingerprint region of 1600, 1500, 1110 and 1026 cm$^{-1}$ and a distribution of weaker less defined absorbances between approximately 630 and 760 cm$^{-1}$.

The "Component Dry Blend" (FIG. 3) has strong absorbances in the fingerprint region of 1560, 1460, 1126 and 756 cm$^{-1}$. Looking closer at its strong absorptions and peak shapes, one skilled in the art would discern that this is indeed a physical blend as both aspects of the independent spectra (FIGS. 1 and 2) are visible yet muted by each other.

Figure 2:
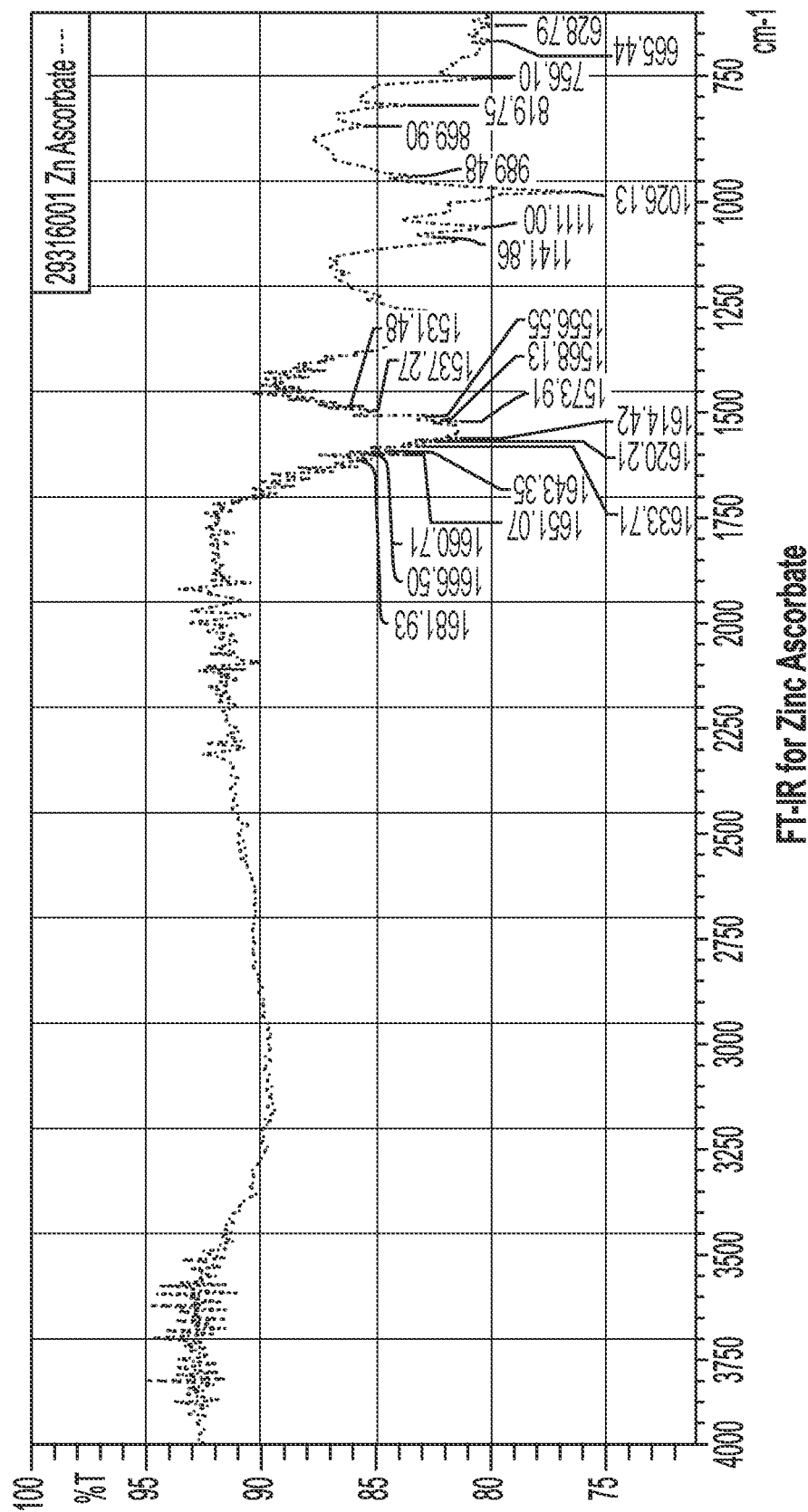
Figure 3:
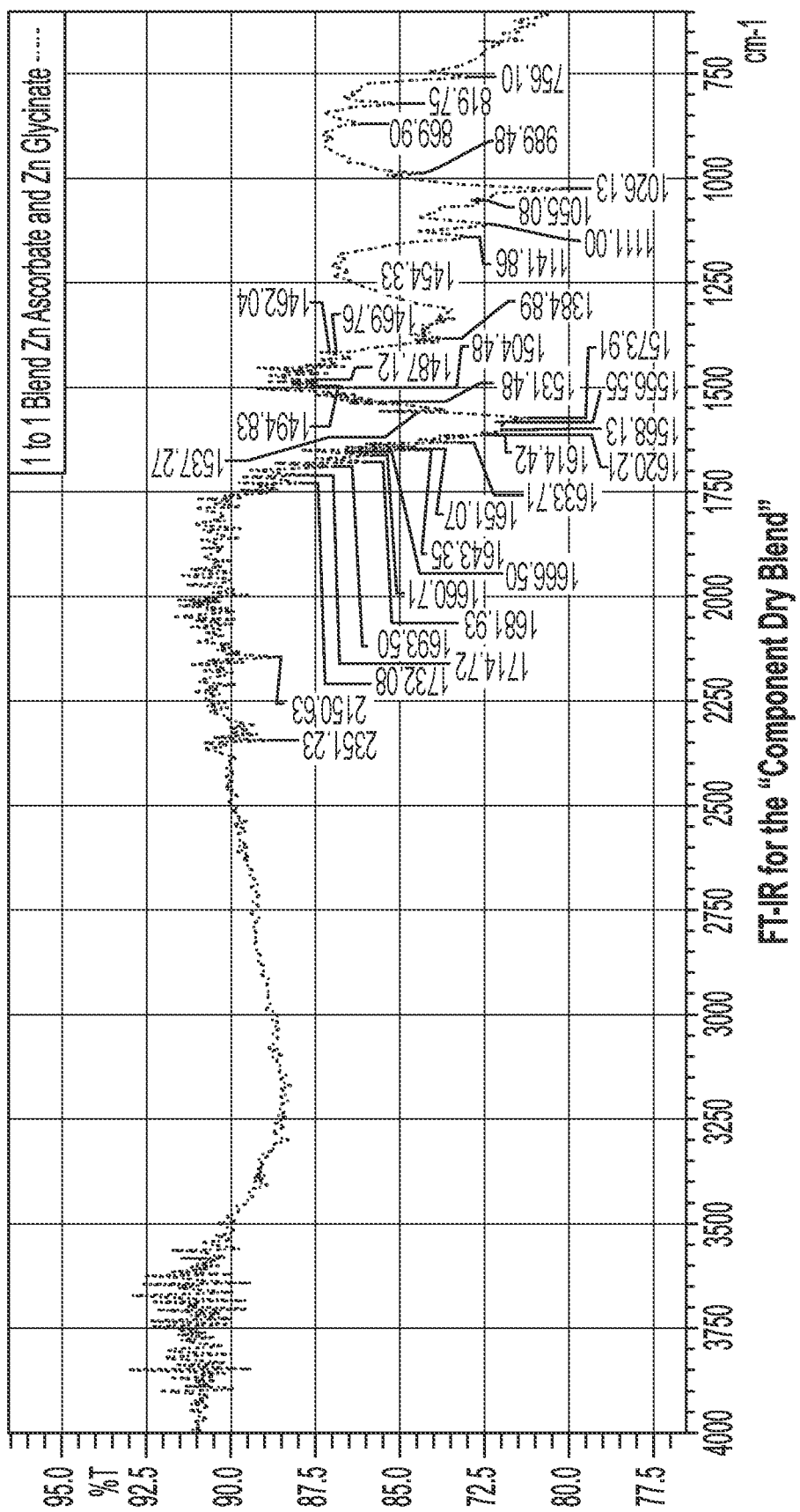
FIG. 3 is an FT-IR spectrum for a "Component Dry Blend" of Zinc Bis-glycinate and Zinc Ascorbate.
Figure 4:
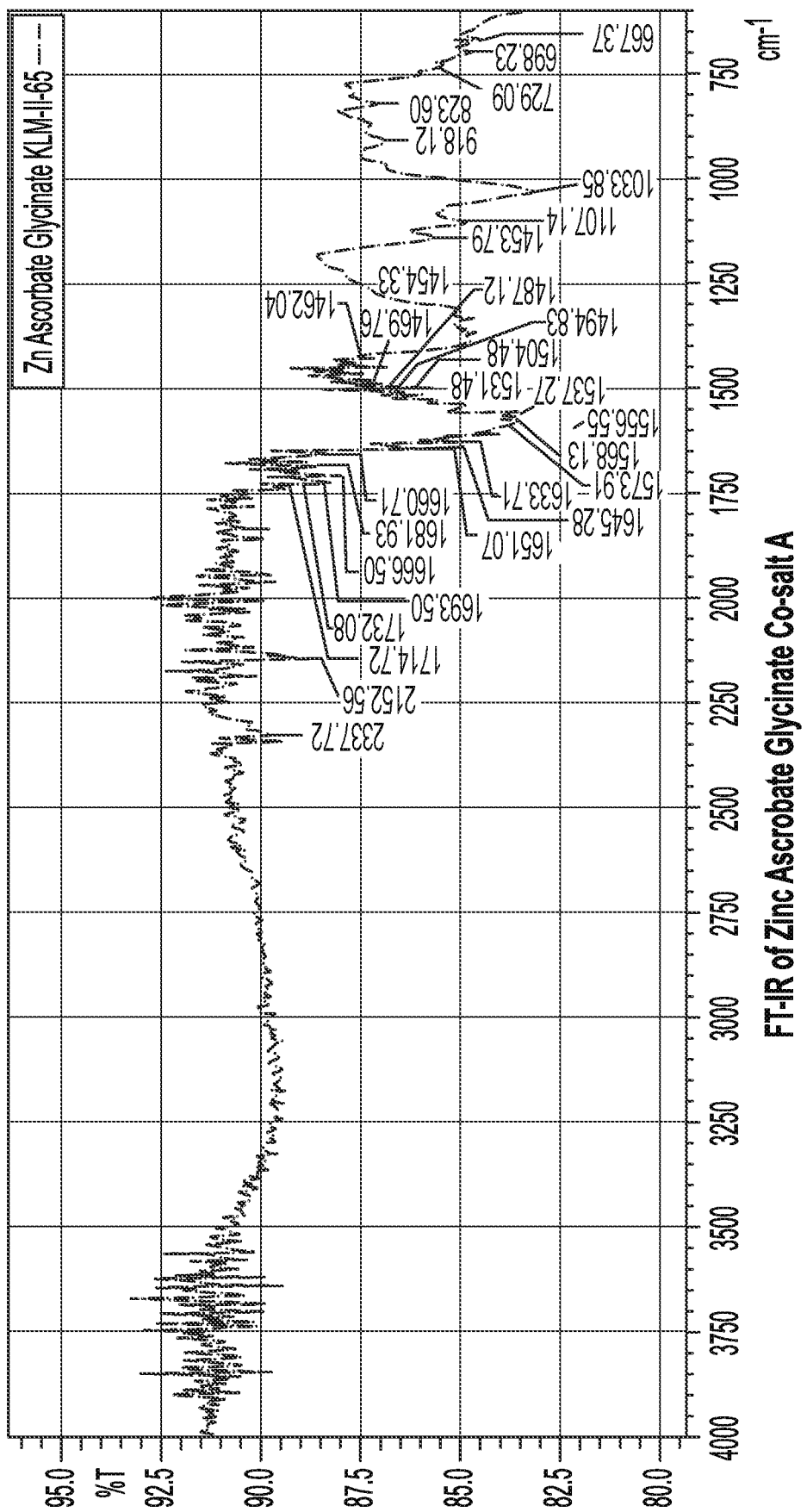
FIGS. 4 and 5 are FT-IR spectrum of Examples A and B, respectively of Zinc Ascorbate Glycinate Co-salt.
Figure 5:
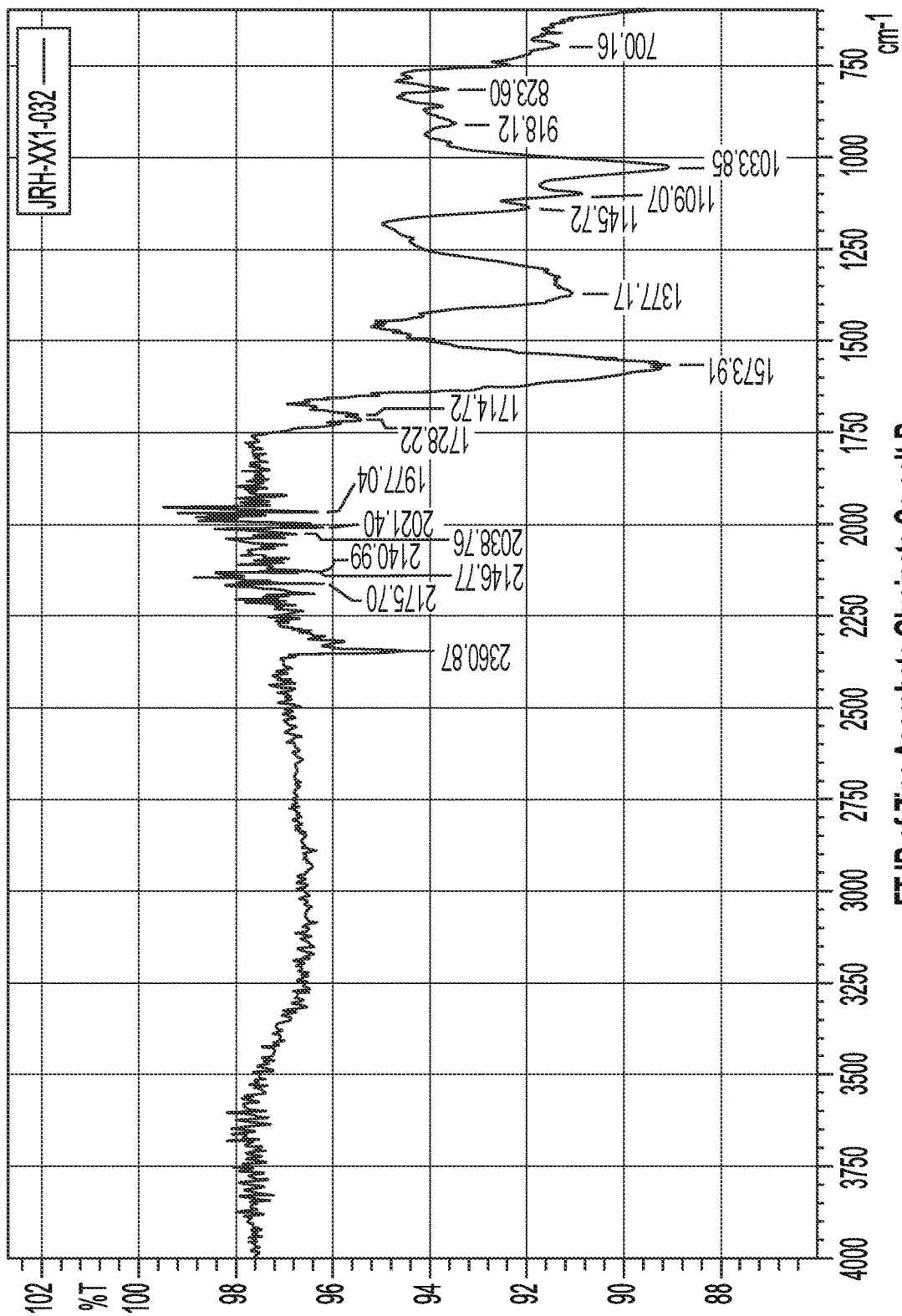

The FT-IR spectrum for zinc ascorbate glycinate co-salt samples A and B are shown in FIGS. 4 and 5. The co-salts have strong yet weakly defined absorbances in the fingerprint region at 1540 and strong broadened absorbances at 1110 and 1030 cm$^{-1}$, taking note that the sharp absorbances between 750-1350 cm$^{-1}$ found in FIGS. 1-3 are either gone have been substantially broadened.

Examination of the FT-IR spectra of the "component dry blend" in FIG. 3 and the zinc ascorbate glycinate co-salts in FIGS. 4 and 5 one skilled in the art will notice that they are substantially different, providing strong evidence that the co-salt is a unique entity and not a mere blend of components.

Particle Morphology by Scanning Electron Microscopy

Figure 6:
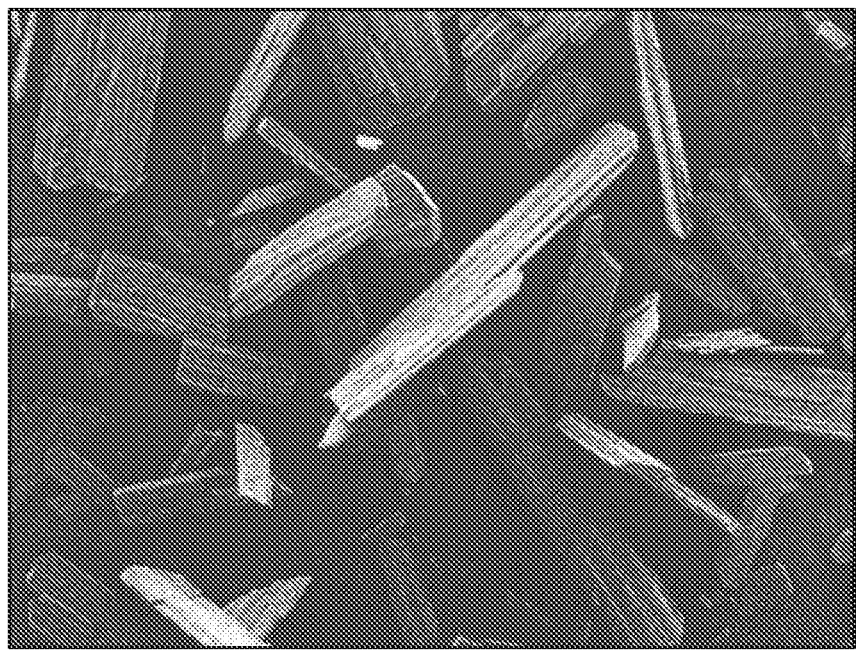
FIGS. 6 and 7 are Scanning Electron Microscope (SEM) images of Zinc Bis-Glycinate and Zinc Ascorbate, respectively.
Figure 7:
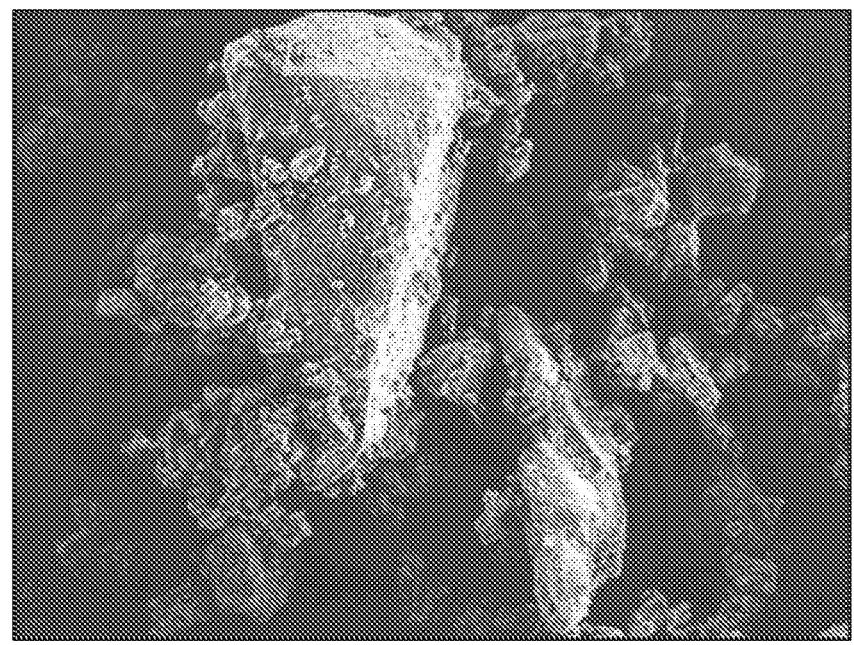
Figure 8:
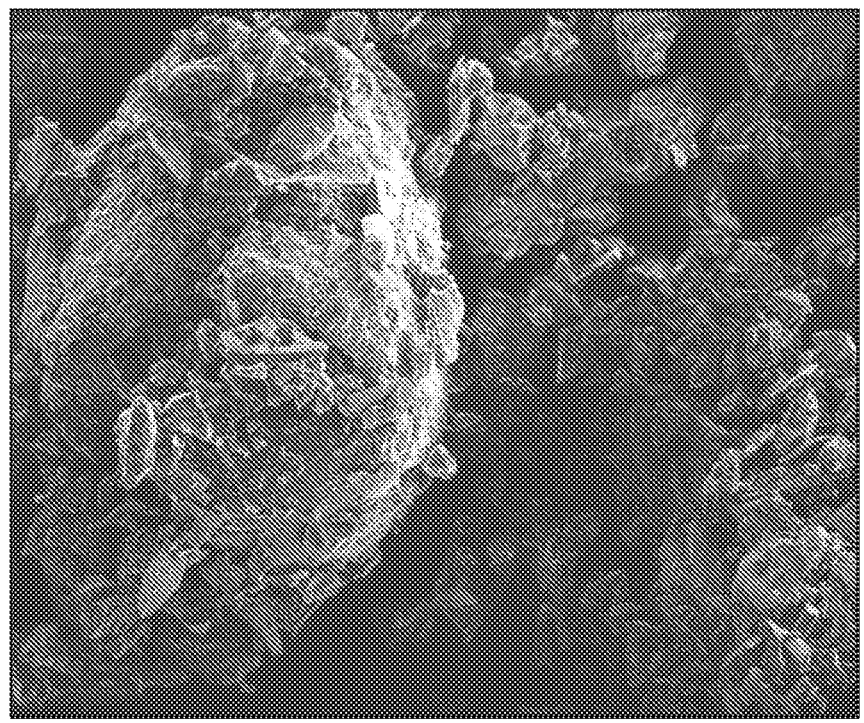
FIG. 8 as an SEM image of Zinc Ascorbate Glycinate Co-Salt.

The unique nature of the zinc ascorbate glycinate co-salt can be both demonstrated and differentiated from magnesium citrate tribasic and magnesium glycinate. FIGS. 6-8 show SEM (Scanning Electron Microscopy) imaging of zinc bis-glycinate, zinc ascorbate and zinc ascorbate glycinate co-salt, respectively.

As shown in FIG. 6, zinc bis-glycinate has a highly crystalline presentation, composed of many rod-shaped crystallites of varying size and orientation. SEM imaging of zinc ascorbate shown in FIG. 7 shows a polymorphic type of crystallinity that is densely packed.

SEM imagery of zinc ascorbate glycinate co-salt, shown in FIG. 8, demonstrates the amorphous nature of this product. One skilled in the art will also realize the porous nature of the solids.

Lack of either the porous polycrystalline crystallites found in zinc ascorbate or rod type crystallites found in zinc bis-glycinate demonstrate that this co-salt is not a mere co-precipitated blend of zinc ascorbate and zinc bis-glycinate, but a unique chemical entity or compound.

X-Ray Diffraction (XRD) Pattern Analysis

Figure 9:
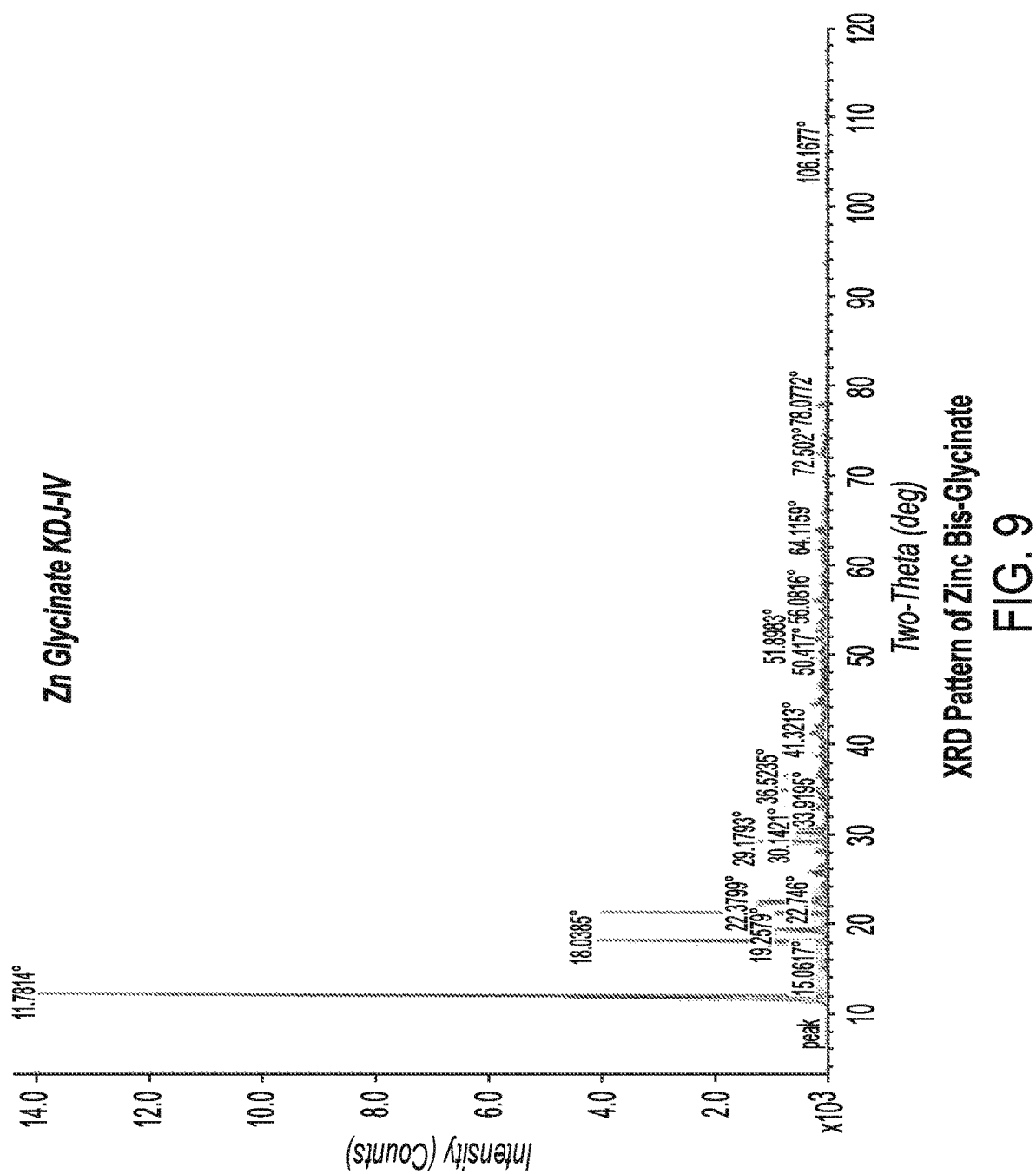
FIGS. 9 and 10 are x-ray diffraction (XRD) Patterns of Zinc Bis-Glycinate and Zinc Ascorbate, respectively.
Figure 10:
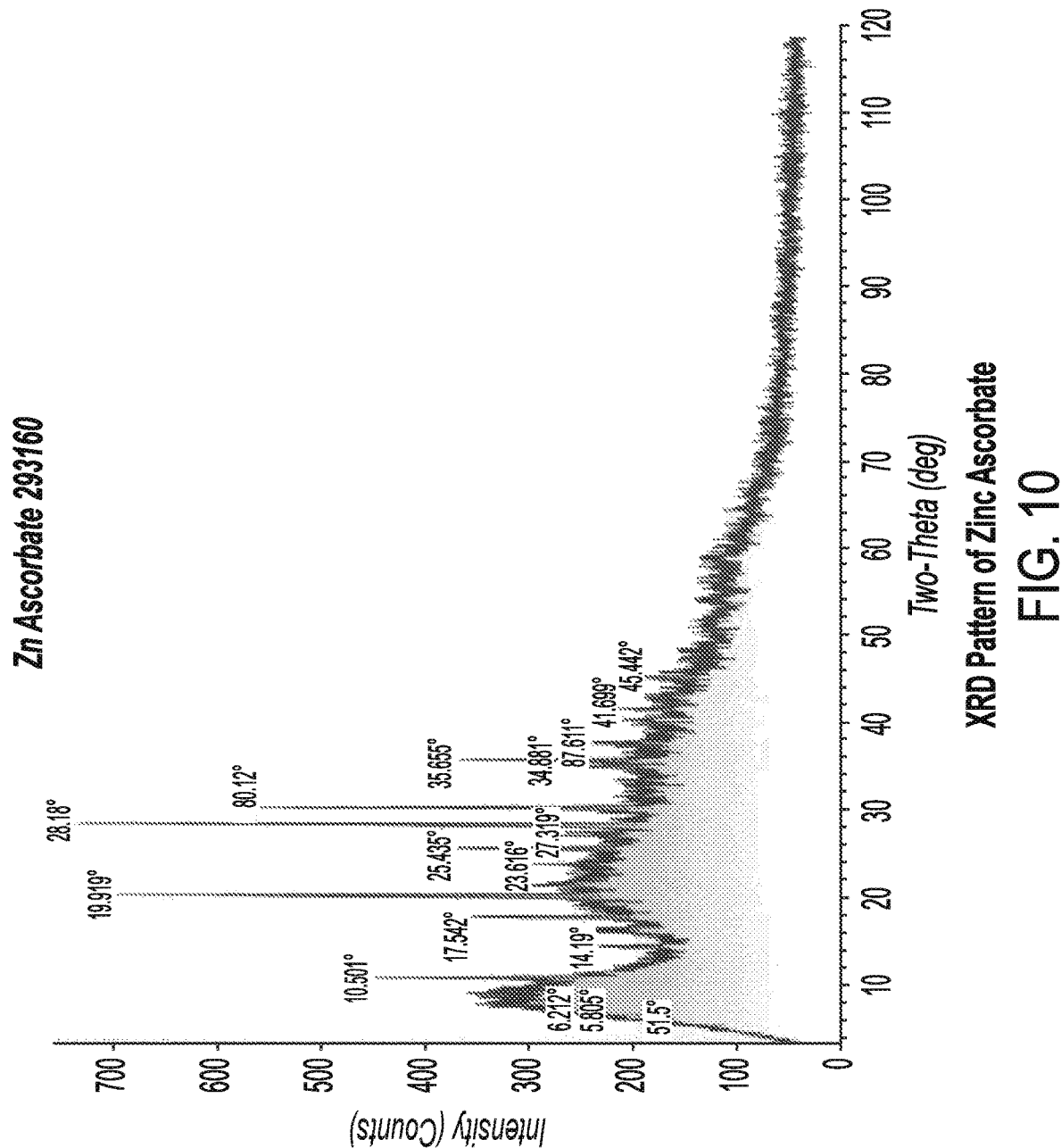

As evidenced from Thermogravimetric Analysis and Particle Morphology by Scanning Electron Microscopy, zinc bis-glycinate and zinc ascorbate are relatively high crystalline materials and as such have very distinct and reproducible XRD patterns as shown in FIGS. 9 and 10. The baseline of the zinc ascorbate XRD pattern is higher and gives less defined theta signals due to the polymorphic nature of the crystals.

Figure 11:
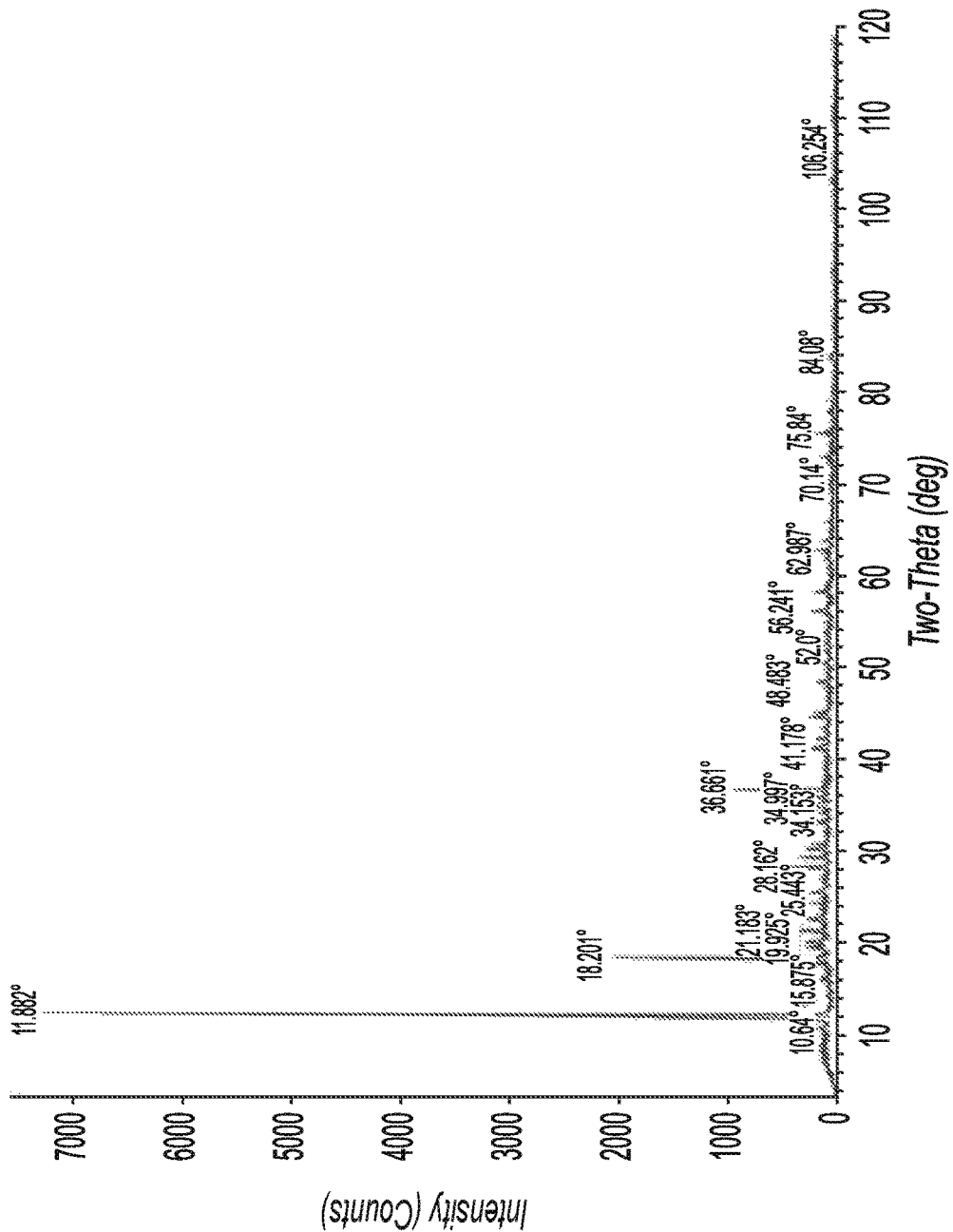
FIG. 11 is an XRD Pattern of the "Component Dry Blend"

The "component dry blend" described above displays distinct high crystalline XRD patterns consistent with both zinc bis-glycinate and zinc ascorbate as shown in FIG. 11.

Figure 12:
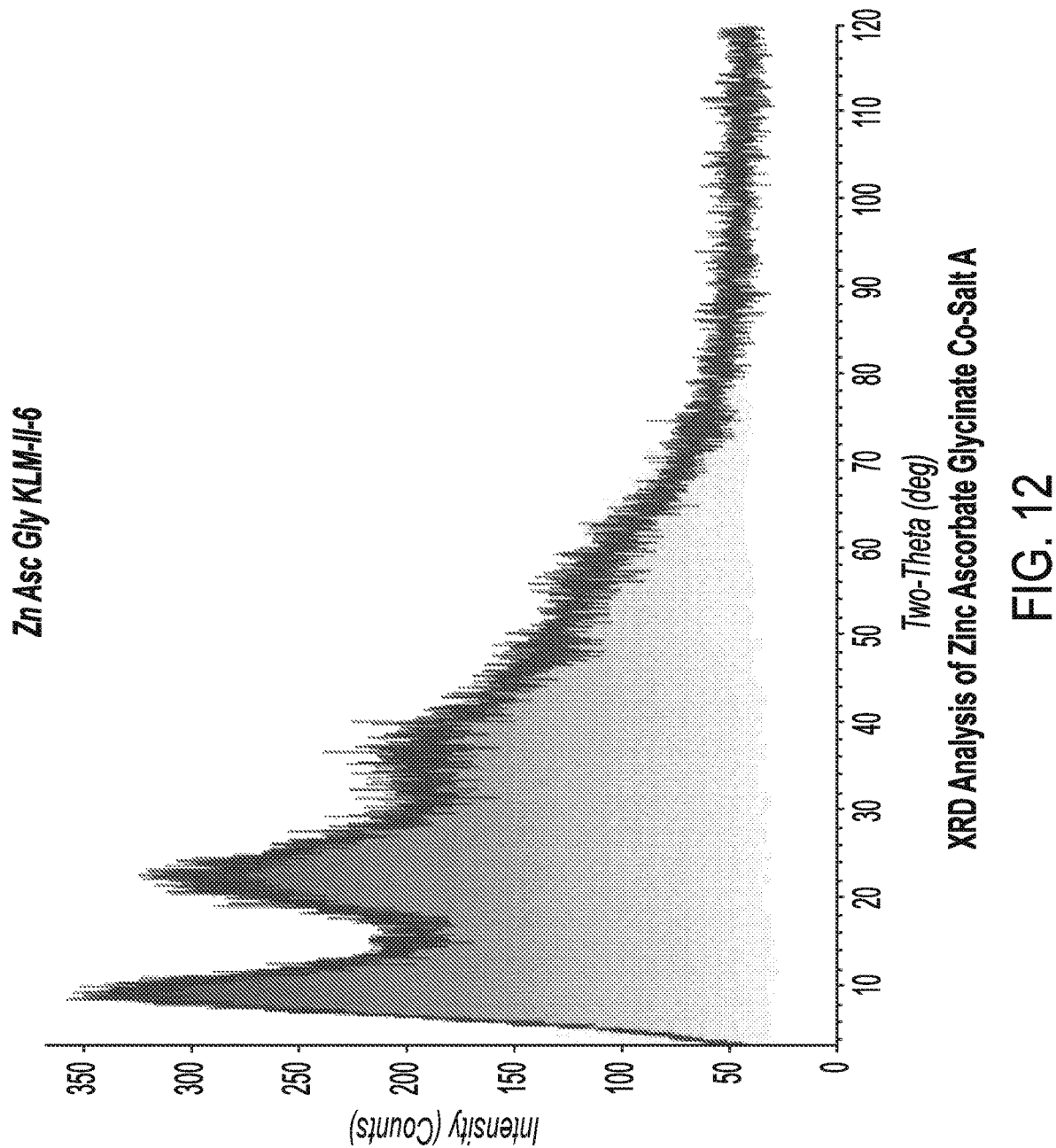
FIGS. 12 and 13 are XRD Analyses of Examples A and B, respectively, of Zinc Ascorbate Glycinate Co-Salt.
Figure 13:
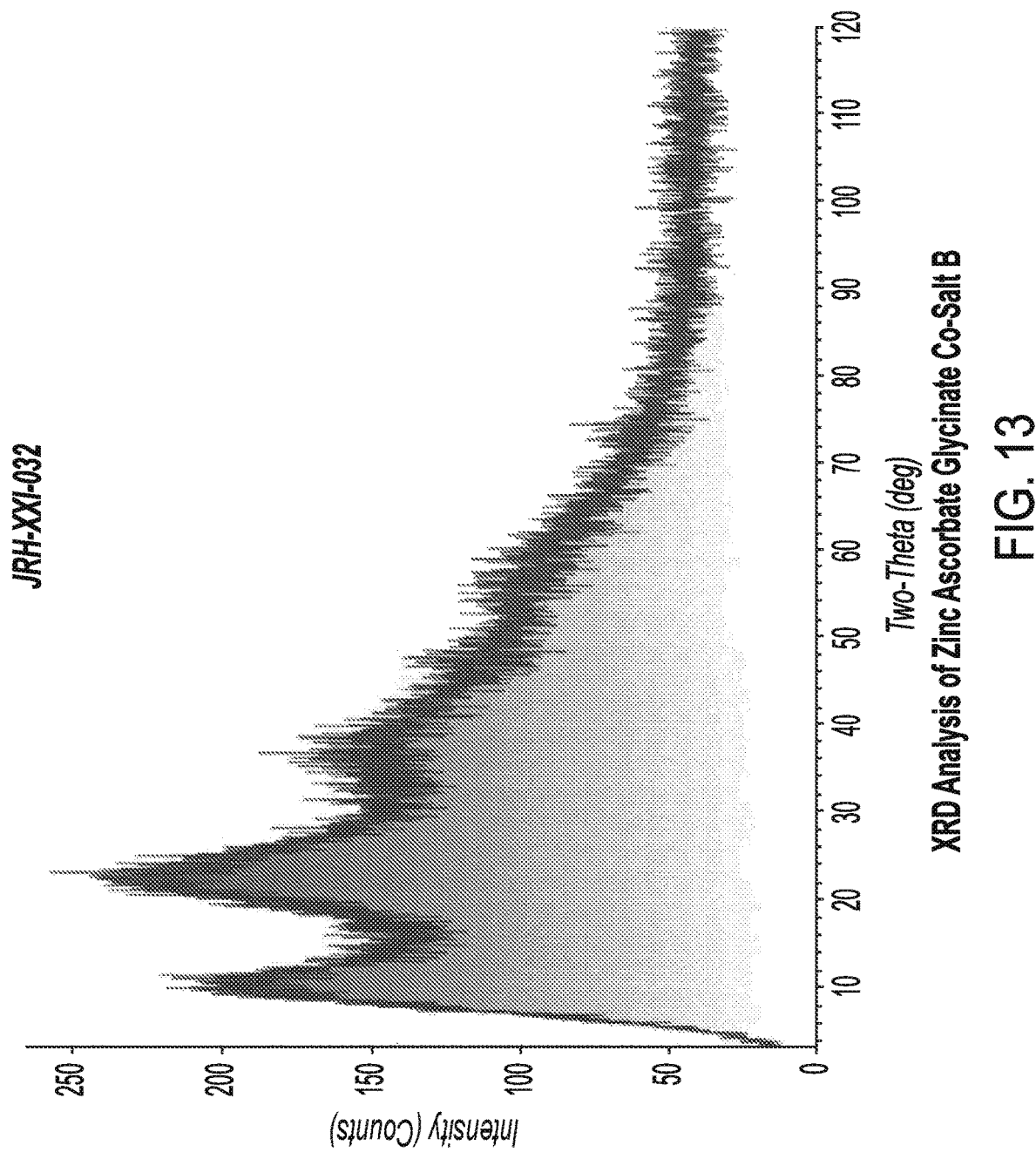

Due to the amorphous nature of zinc ascorbate glycinate co-salt as evidenced from Particle Morphology by Scanning Electron Microscopy, this compound does not show any degree of crystallinity by XRD as shown in FIGS. 12 and 13. The fact that the "component dry blend" shows both zinc bis-glycinate and zinc ascorbate theta signals and the zinc ascorbate glycinate co-salt does not, provides strong evidence that the zinc ascorbate glycinate co-salt is a unique entity and not a mere blend of components.

Zinc Ascorbate Glycinate Solubility Experiment

It was discovered that zinc ascorbate glycinate co-salt was soluble in acetone, but zinc ascorbate, zinc bisglycinate and glycine were not. This is further evidence that zinc ascorbate glycinate has distinct properties from zinc ascorbate, zinc bisglycinate and glycine. Zinc ascorbate glycinate co-salt is a unique compound and not a mixture of bi-products or raw materials.

2. Calcium Ascorbate Glycinate Co-Salt

A typical lab scale (1 mol scale) preparation of calcium ascorbate glycinate co-salt was prepared as follows: A reaction mixture was prepared comprising 176.12 g (1 mol) anhydrous ascorbic acid and 75.01 g (1 mol) glycine dissolved in 1000 g of water. The mixture was heated to 60-80° C. The resulting acid solution was neutralized with 75.6 g (1 mol) of ultra-pure calcium hydroxide (to avoid any decomposition of ascorbic acid due to trace iron or copper impurities) and digested with agitation at 60-80° C. until complete reaction was achieved, between 1-4 hours. The resulting reaction mass contained 289.25 g (1 mol) of calcium ascorbate glycinate co-salt having a metal to ligand ratio of 1:1:1 remaining in solution. The reaction mass was filtered to remove any unreacted calcium hydroxide and other extraneous matter. The filtrate was dried to produce a free-flowing beige to yellow powder containing calcium ascorbate glycinate co-salt having a metal to ligand ratio of 1:1:1 and a moisture content of 0.0-20.0%.

Figure 14:
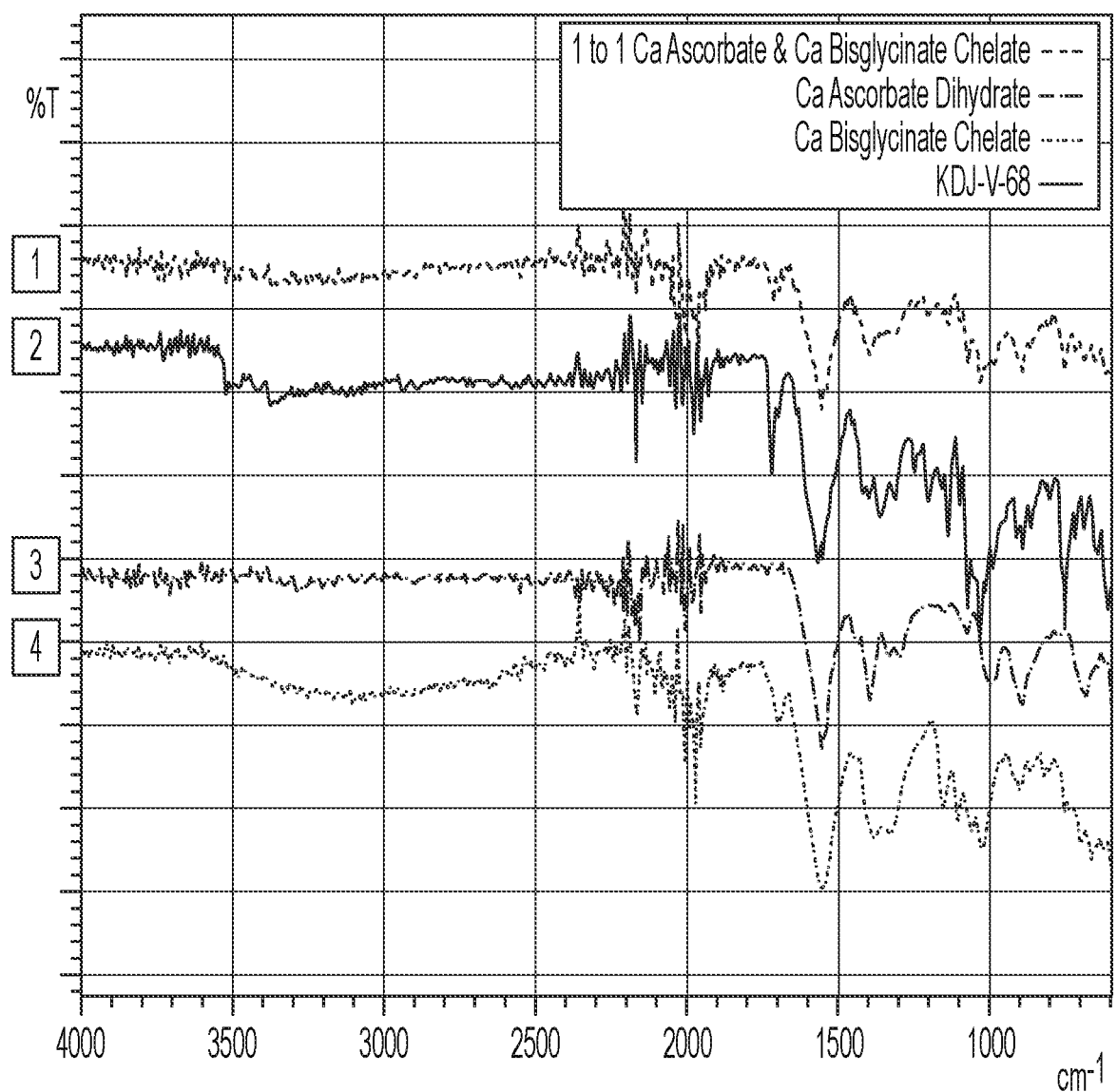
FIG. 14 is a chart of FT-IR spectra comparing calcium ascorbate glycinate co-salt, calcium ascorbate, calcium bisglycinate, and a 1:1 dry mix of calcium ascorbate and calcium bisglycinate.
Figure 15A:
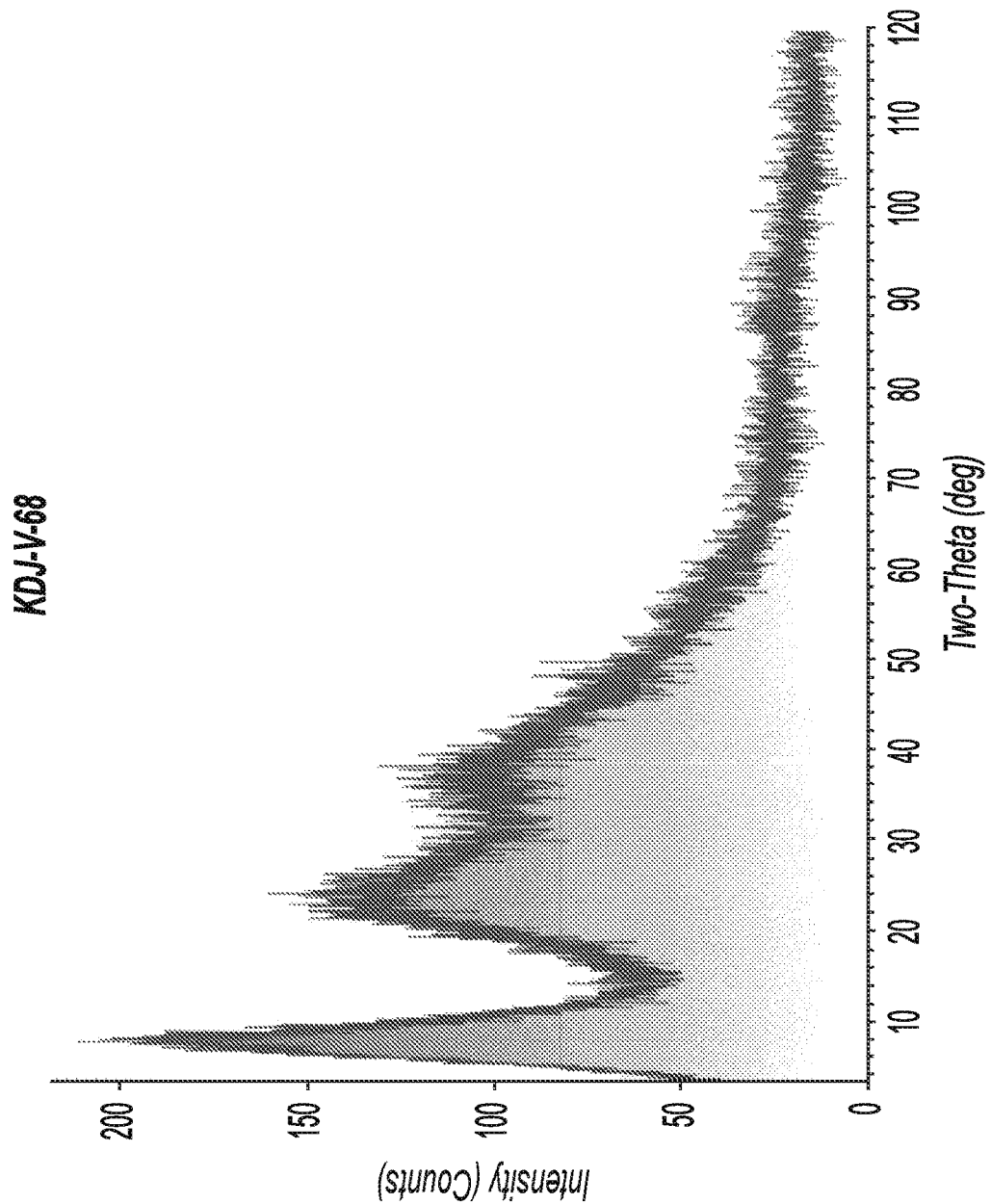
Figure 15B:
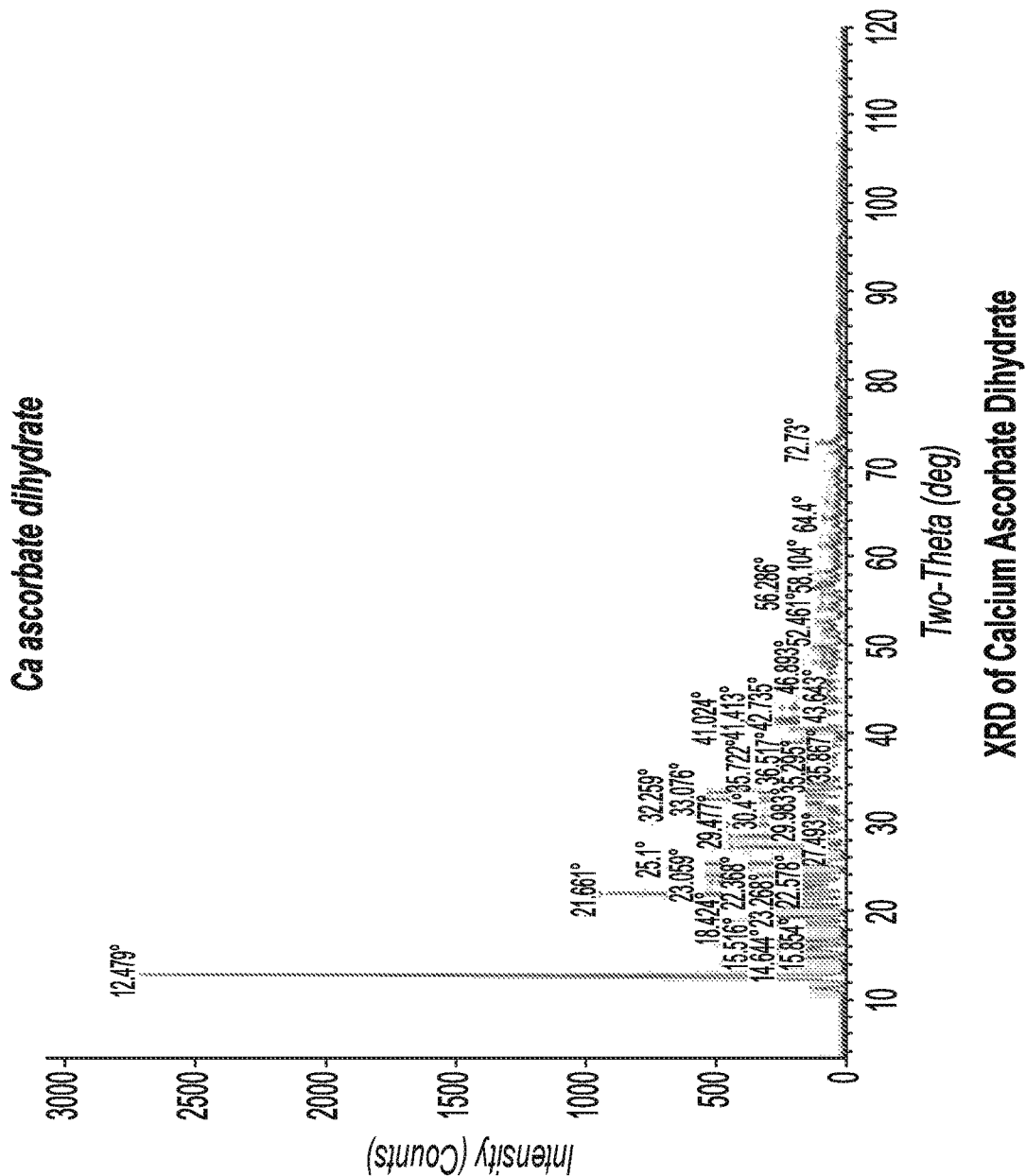
Figure 15C:
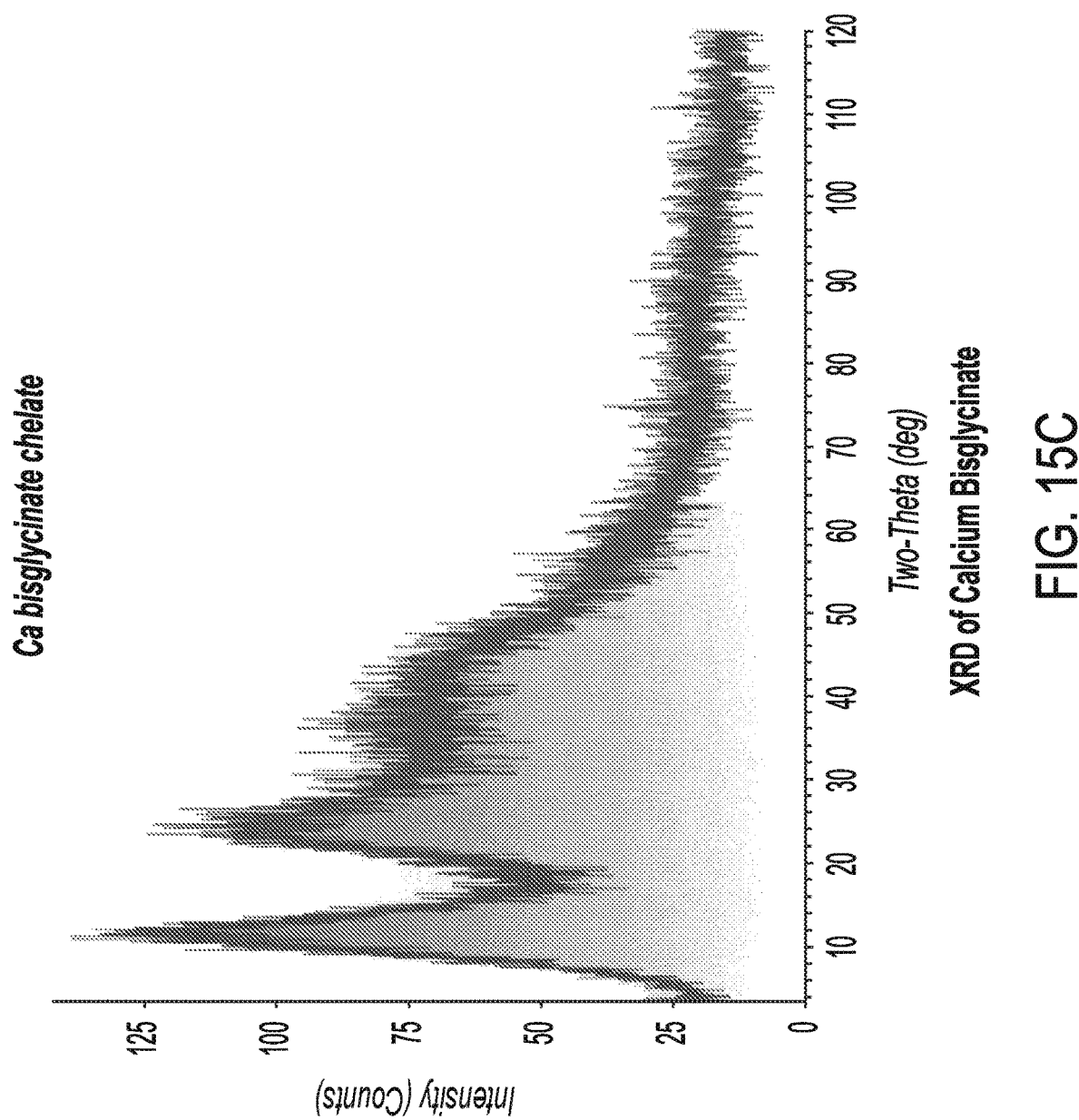

Table 3 below shows analytical data for the calcium ascorbate glycinate produced above, and FIG. 14 shows FT-IR spectra comparisons for the calcium ascorbate glycinate co-salt vs. calcium ascorbate, calcium bisglycinate and a 1:1 dry mix of calcium ascorbate and calcium bisglycinate. FIGS. 15A-D show XRD patterns of the calcium ascorbate glycinate co-salt vs. calcium ascorbate, calcium bisglycinate and a 1:1 dry mix of calcium ascorbate and calcium bisglycinate.

TABLE 3

| % Ca (theo. 13.9%) Spec = 13.6-14.2% | % Water Spec = 0-20% | % Ascorbic Acid (theo. 60.5%) Spec = 48.4-61.7% |
|---|---|---|
| 14.2% | 9.0% | 56.7% |

FIG. 14 shows the FT-IR comparisons of Calcium Ascorbate Glycinate co-salt (line 4), calcium ascorbate (line 2), calcium bisglycinate (line 3) and a 1:1 dry mix of calcium ascorbate and calcium bisglycinate (line 1). As seen, the co-salt produces an FT-IR spectrum different from calcium ascorbate, calcium glycinate, and 1:1 mix of calcium ascorbate and calcium glycinate. FIGS. 15A-D show XRD patterns for Calcium Ascorbate Glycinate co-salt, calcium ascorbate, calcium bisglycinate and a 1:1 dry mix of calcium ascorbate and calcium bisglycinate, respectively. Again, as seen, the XRD pattern for the co-salt is different from the XRD patterns for calcium ascorbate, calcium glycinate, and 1:1 mix of calcium ascorbate and calcium glycinate. These comparisons show that the co-salt is a unique compound and not a mixture of bi-products or raw materials.

3. Magnesium Ascorbate Glycinate

A typical lab scale (1 mol scale) preparation of magnesium ascorbate glycinate co-salt follows: A reaction mixture was prepared comprising 176.12 g (1 mol) anhydrous ascorbic acid and 75.01 g (1 mol) glycine dissolved in 1000 g of water. The mixture was heated to 60-80° C. The resulting acid solution was neutralized with 41.1 g (1 mol) of ultra-pure magnesium oxide (to avoid any decomposition of ascorbic acid due to trace iron or copper impurities) and digested with agitation at 60-80° C. until complete reaction was achieved between 1-4 hours. The resulting reaction mass contained 273.48 g of magnesium ascorbate glycinate co-salt having a metal to ligand ratio of 1:1:1 remaining in solution. The reaction mass was filtered to remove any unreacted magnesium oxide and other extraneous matter. The filtrate was dried to produce a free-flowing yellow to butterscotch colored powder containing magnesium ascorbate glycinate co-salt having a metal to ligand ratio of 1:1:1 and a moisture content of 0.0-20.0%.

Figure 16:
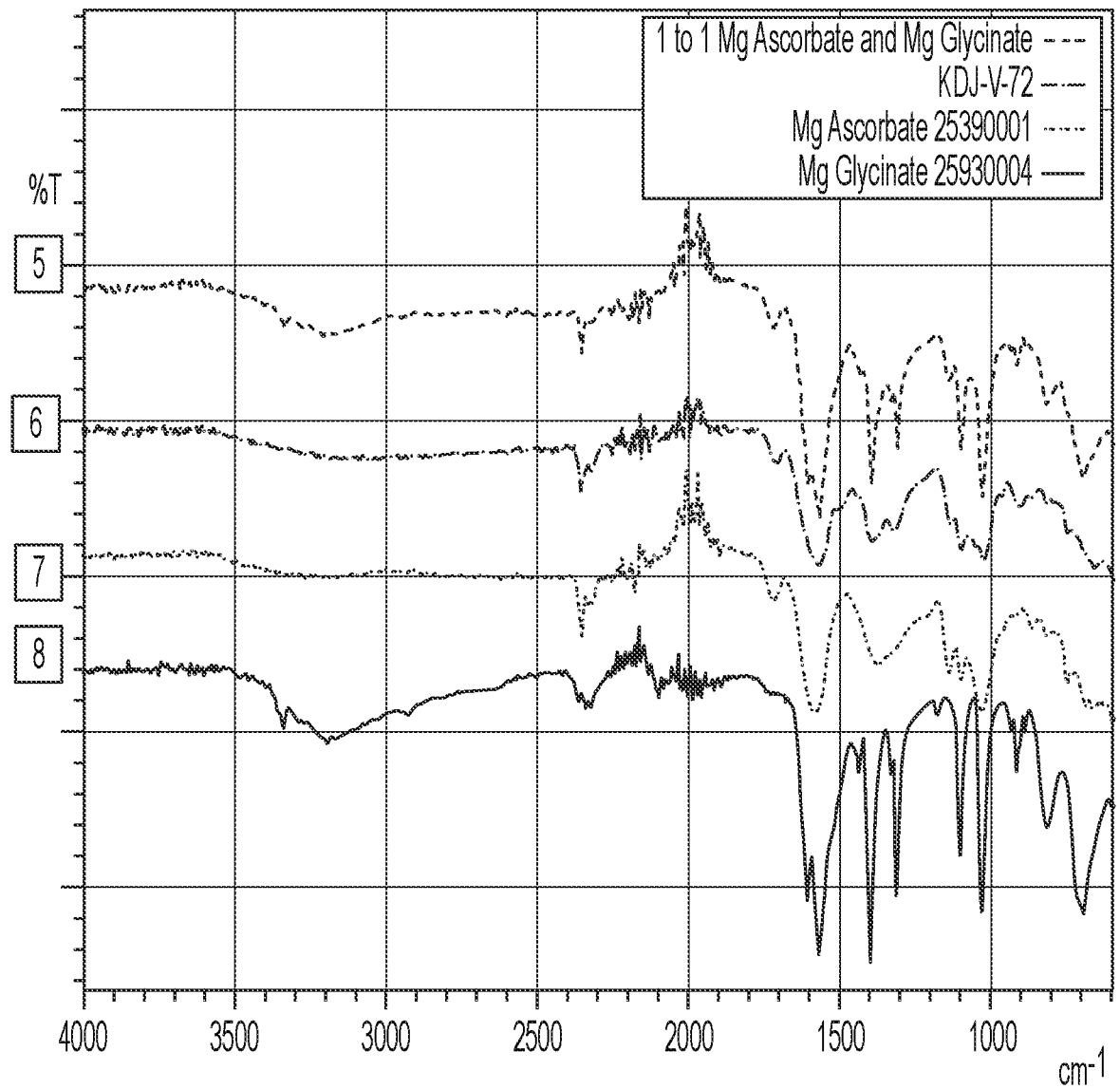
FIG. 16 is a chart of FT-IR spectra comparing magnesium ascorbate glycinate co-salt, Magnesium ascorbate, Magnesium bisglycinate, and a 1:1 dry mix of magnesium ascorbate and magnesium bisglycinate.
Figure 17A:
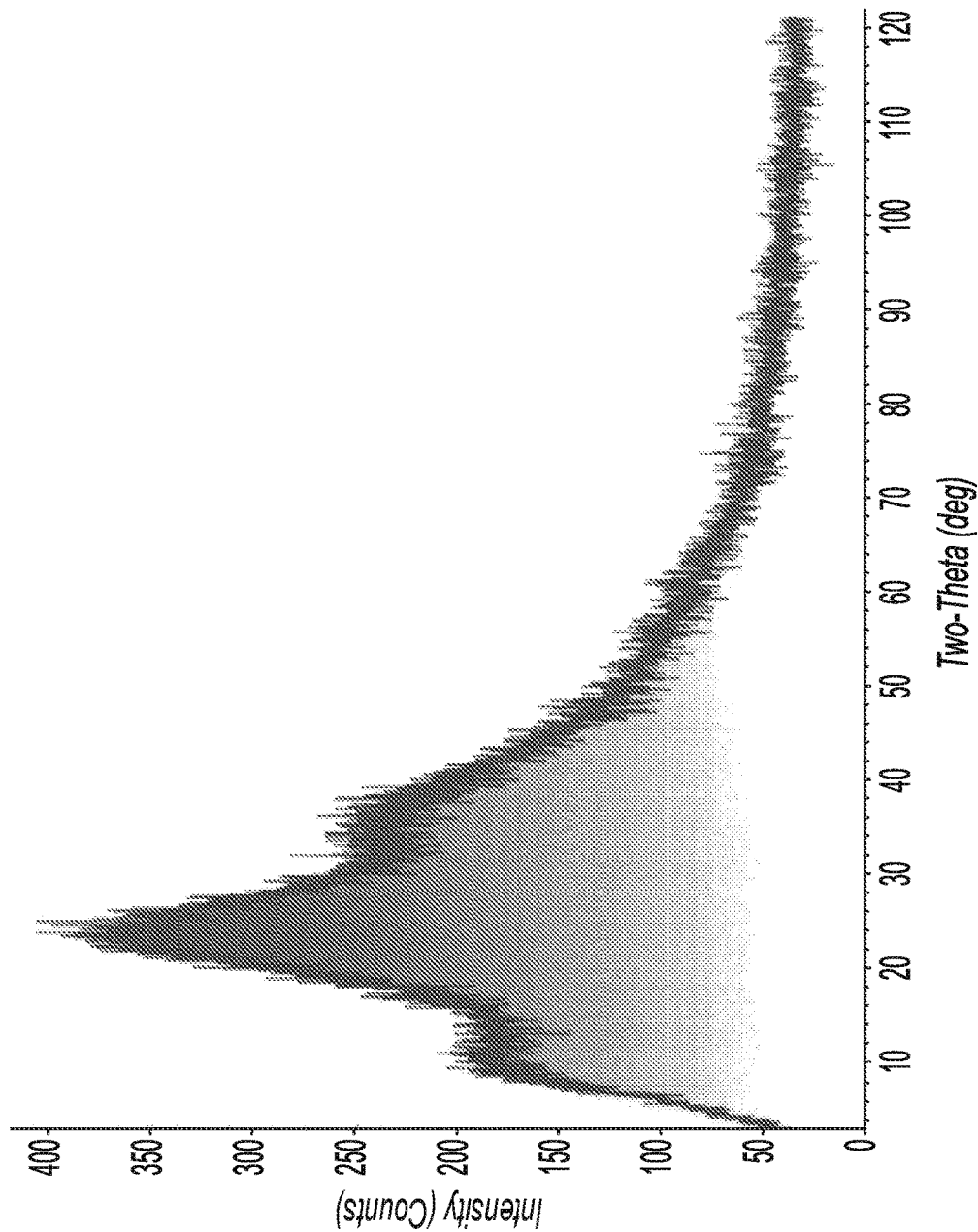
Figure 17B:
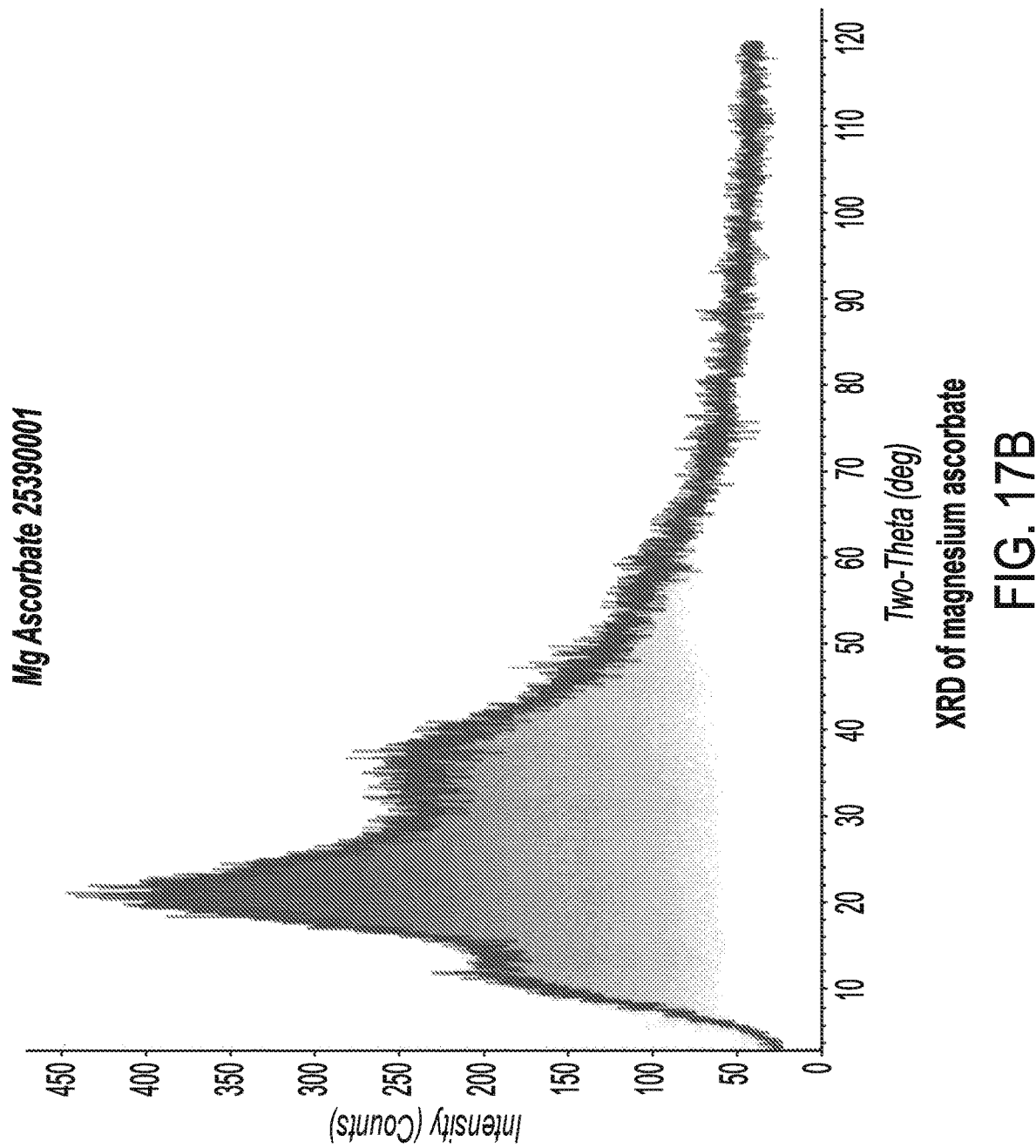
Figure 17C:
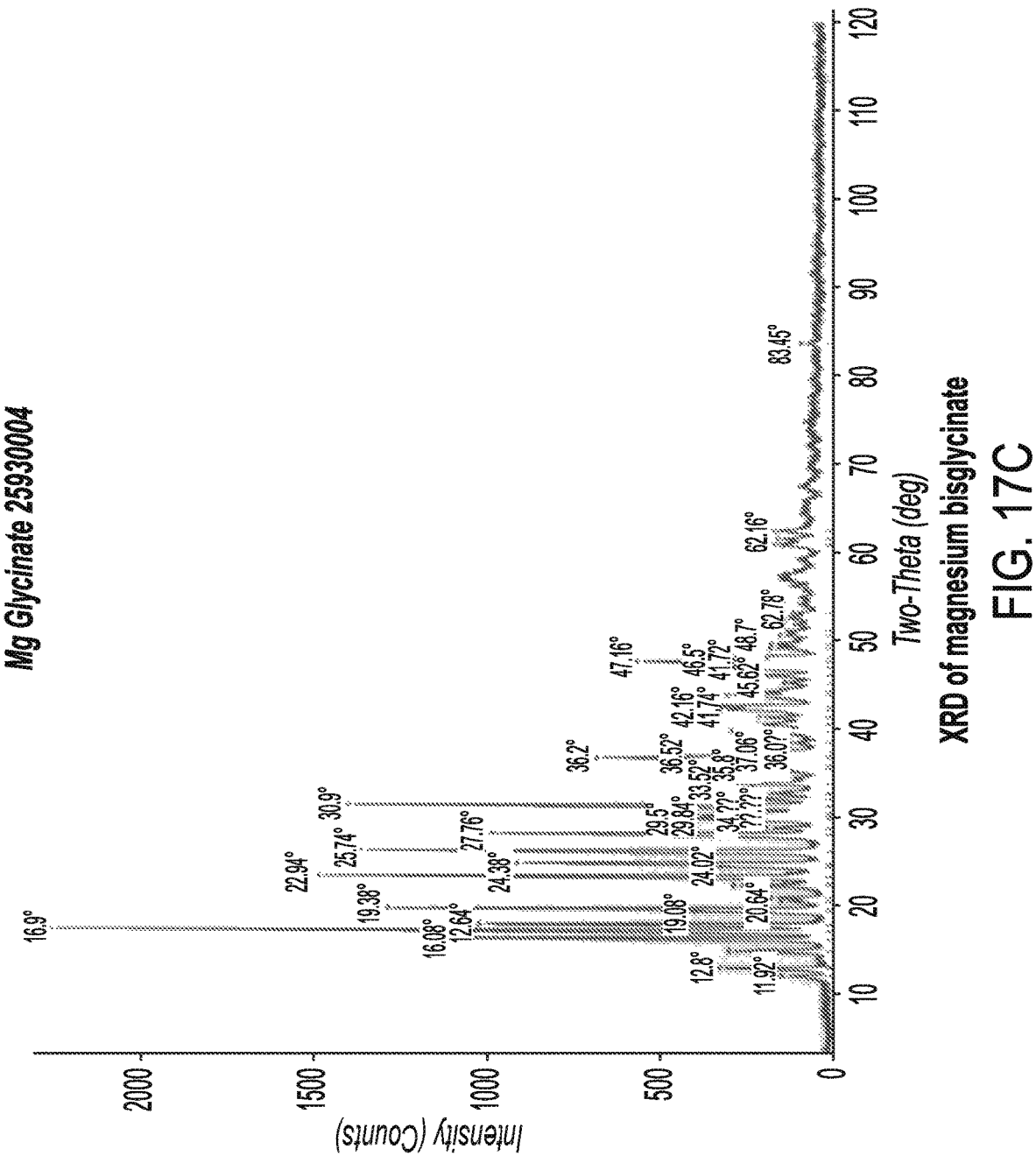

Table 4 below shows analytical data for magnesium ascorbate glycinate. FIG. 16 shows FT-IR spectra comparing magnesium ascorbate glycinate co-salt vs. magnesium ascorbate, magnesium bisglycinate and a 1:1 dry mix of magnesium ascorbate and magnesium bisglycinate. FIGS. 17A-D show XRD patterns of magnesium ascorbate glycinate co-salt vs. magnesium ascorbate, magnesium bisglycinate and a 1:1 dry mix of magnesium ascorbate and magnesium bisglycinate.

TABLE 4

| Mg Source | % Mg (theo. 8.9%) Spec = 8.7-9.1% | % Water (0-20%) | % Ascorbic Acid (theo. 64.4%) Spec = 51.5-65.7% |
|---|---|---|---|
| MgO | 8.7% | 15.3% | 60.7% |

FIG. 16 shows the FT-IR spectra comparisons of magnesium ascorbate glycinate co-salt (line 6), Magnesium ascorbate (line 7), Magnesium bisglycinate (line 8) and a 1:1 dry mix of magnesium ascorbate and calcium bisglycinate (line 5). As seen, the co-salt produces an FT-IR spectrum different from magnesium ascorbate, magnesium glycinate, and 1:1 mix of magnesium ascorbate and magnesium glycinate. FIGS. 17A-D show XRD patterns for magnesium ascorbate glycinate co-salt, magnesium ascorbate, magnesium bisglycinate, and a 1:1 dry mix of Magnesium ascorbate and Magnesium bisglycinate, respectively. Again, as seen, the XRD pattern for the co-salt is different from the XRD patterns for magnesium ascorbate, magnesium glycinate, and 1:1 mix of magnesium ascorbate and magnesium glycinate. These comparisons show that the co-salt is a unique compound and not a mixture of bi-products or raw materials.

In view of the above, it will be seen that the several objects and advantages of the present invention have been achieved and other advantageous results have been obtained.

As various changes could be made in the above constructions without departing from the scope of the invention, it is intended that all matter contained in the above description or shown in the accompanying drawings shall be interpreted as illustrative and not in a limiting sense.

REFERENCES

1. Mossad S, Macknin M, Mendendorp S, et al. Zinc Gluconate Lozenges for Treating the Common Cold: A Randomized, Double-Blind, Placebo-Controlled Study. Annals of Internal Medicine 15 Jul. 1996
2. to Velthuis A J W, van den Worm S H E, Sims A C, Baric R S, Snijder E J, van Hemert M J (2010) $Zn^{2+}$ Inhibits Coronavirus and Arterivirus RNA Polymerase Activity In Vitro and Zinc Ionophores Block the Replication of These Viruses in Cell Culture. PLoS Pathog 6(11): e1001176.
3. Shankar A H, Prasad A S. Zinc, and immune function: the biological basis of altered resistance to infection. Am J Clin Nutr. 1998 August; 68(2 Suppl):4475-4635.
4. Singh M, Das R R. Zinc for the common cold. Cochrane Database of Systematic Reviews 2013, Issue 6. Art. No.: CD001364. DOI: 10.1002/14651858.CD001364.pub4.
5. Liguori, I., Russo, G., Curcio, F., Bulli, G., Aran, L., Della-Morte, D., Gargiulo, G., Testa, G., Cacciatore, F., Bonaduce, D., & Abete, P. (2018). Oxidative stress, aging, and diseases. Clinical interventions in aging, 13, 757-772.
6. Persaud, C., Forrester, T., & Jackson, A. A. (1996). Urinary excretion of 5-L-oxoproline (pyroglutamic acid) is increased during recovery from severe childhood malnutrition and responds to supplemental glycine. The Journal of nutrition, 126(11), 2823-2830.
7. McCarty, M. F., O'Keefe, J. H., & DiNicolantonio, J. J. (2018). Dietary Glycine Is Rate-Limiting for Glutathione Synthesis and May Have Broad Potential for Health Protection. The Ochsner journal, 18(1), 81-87.
8. Branch J. D. (2003). Effect of creatine supplementation on body composition and performance: a meta-analysis. International journal of sport nutrition and exercise metabolism, 13(2), 198-226. https://doi.org/10.1123/ijsnem.13.2.198
9. Chilibeck, P. D., Kaviani, M., Candow, D. G., & Zello, G. A. (2017). Effect of creatine supplementation during resistance training on lean tissue mass and muscular strength in older adults: a meta-analysis. Open access journal of sports medicine, 8, 213-226. https://doi.org/10.2147/OAJSM.S123529
10. Lanhers, C., Pereira, B., Naughton, G., Trousselard, M., Lesage, F. X., & Dutheil, F. (2017). Creatine Supplementation and Upper Limb Strength Performance: A Systematic Review and Meta-Analysis. Sports medicine (Auckland, N.Z.), 47(1), 163-173. https://doi.org/10.1007/s40279-016-0571-4
11. Chilibeck, P. D., Candow, D. G., Landeryou, T., Kaviani, M., & Paus-Jenssen, L. (2015). Effects of Creatine and Resistance Training on Bone Health in Postmenopausal Women. Medicine and science in sports and exercise, 47(8), 1587-1595.
12. Avgerinos, K. I., Spyrou, N., Bougioukas, K. I., & Kapogiannis, D. (2018). Effects of creatine supplementation on cognitive function of healthy individuals: A systematic review of randomized controlled trials. Experimental gerontology, 108, 166-173.
13. Krei3der, R. B., Kalman, D. S., Antonio, J., Ziegenfuss, T. N., Wildman, R., Collins, R., Candow, D. G., Kleiner, S. M., Almada, A. L., & Lopez, H. L. (2017). International Society of Sports Nutrition position stand: safety and efficacy of creatine supplementation in exercise, sport, and medicine. Journal of the International Society of Sports Nutrition, 14, 18.
14. Kalhan, S. C., Gruca, L., Marczewski, S., Bennett, C., & Kummitha, C. (2016). Whole body creatine and protein kinetics in healthy men and women: effects of creatine and amino acid supplementation. Amino acids, 48(3), 677-687.
15. González-Ortiz, M., Medina-Santillan, R., Martínez-Abundis, E., & von Drateln, C. R. (2001). Effect of glycine on insulin secretion and action in healthy first-degree relatives of type 2 diabetes mellitus patients. Hormone and metabolic research=Hormon- und Stoffwechselforschung=Hormones et metabolisme, 33(6), 358-360.
16. Proksch, E., Segger, D., Degwert, J., Schunck, M., Zague, V., & Oesser, S. (2014). Oral supplementation of specific collagen peptides has beneficial effects on human skin physiology: a double-blind, placebo-controlled study. Skin pharmacology and physiology, 27(1), 47-55.
17. Clark, K. L., Sebastianelli, W., Flechsenhar, K. R., Aukermann, D. F., Meza, F., Millard, R. L., Deitch, J. R., Sherbondy, P. S., & Albert, A. (2008). 24-Week study on the use of collagen hydrolysate as a dietary supplement in athletes with activity-related joint pain. Current medical research and opinion, 24(5), 1485-1496. https://doi.org/10.1185/030079908x291967
18. Elam, M. L., Johnson, S. A., Hooshmand, S., Feresin, R. G., Payton, M. E., Gu, J., & Arjmandi, B. H. (2015). A calcium-collagen chelate dietary supplement attenuates bone loss in postmenopausal women with osteopenia: a randomized controlled trial. Journal of medicinal food, 18(3), 324-331. https://doi.org/10.1089/jmf.2014.0100
19. Bannai, M., & Kawai, N. (2012). New therapeutic strategy for amino acid medicine: glycine improves the quality of sleep. Journal of pharmacological sciences, 118(2), 145-148.
20. Kawai, N., Sakai, N., Okuro, M., Karakawa, S., Tsuneyoshi, Y., Kawasaki, N., Takeda, T., Bannai, M., & Nishino, S. (2015). The sleep-promoting and hypothermic effects of glycine are mediated by NMDA receptors in the suprachiasmatic nucleus. Neuropsychopharmacology: official publication of the American College of Neuropsychopharmacology, 40(6), 1405-1416.
21. Yamadera, W., Inagawa, K., Chiba, S. et al. Glycine ingestion improves subjective sleep quality in human volunteers, correlating with polysomnographic changes. *Sleep Biol. Rhythms* 5, 126-131 (2007).

22. Inagawa, K., Hiraoka, T., Kohda, T. et al. Subjective effects of glycine ingestion before bedtime on sleep quality. *Sleep Biol. Rhythms* 4, 75-77 (2006). https://doi.org/10.1111/j.1479-8425.2006.00193.x

The invention claimed is:

1. A divalent Metal Ascorbate Glycinate Co-Salt having a formula of $MC_8H_{11}NO_8$, where M is a divalent cation of Ca, Mg, or Zn.

2. The divalent metal ascorbate glycinate co-salt of claim 1 having the structure of:

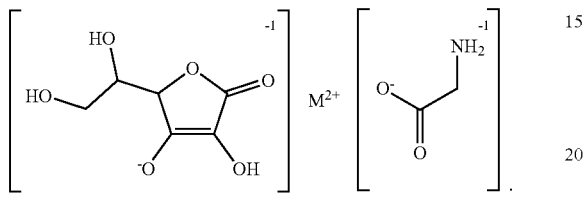

3. The divalent metal ascorbate glycinate co-salt of claim 1 having a metal content of about 8% to about 21% on an anhydrous basis.

4. The divalent metal ascorbate glycinate co-salt of claim 1 being a powder and containing between 0.0-20.0% water.

* * * * *